(12) United States Patent
Zhang et al.

(10) Patent No.: US 11,475,979 B2
(45) Date of Patent: Oct. 18, 2022

(54) METHOD, APPARATUS, AND COMPUTER-READABLE MEDIUM FOR PREDICTING A HYBRIDIZATION RATE CONSTANT OF A FIRST SEQUENCE

(71) Applicants: Xuemeng Zhang, Houston, TX (US); Zheng Fang, Houston, TX (US); Ruojia Wu, Houston, TX (US); Wei Duan, Beijing (CN); David Zhang, Houston, TX (US); William Marsh Rice University, Houston, TX (US)

(72) Inventors: Xuemeng Zhang, Houston, TX (US); Zheng Fang, Houston, TX (US); Ruojia Wu, Houston, TX (US); Wei Duan, Beijing (CN); David Zhang, Houston, TX (US)

(73) Assignee: William Marsh Rice University, Houston, TX (US)

( * ) Notice: Subject to any disclaimer, the term of this patent is extended or adjusted under 35 U.S.C. 154(b) by 739 days.

(21) Appl. No.: 16/308,346

(22) PCT Filed: Jun. 7, 2017

(86) PCT No.: PCT/US2017/036410
§ 371 (c)(1),
(2) Date: Dec. 7, 2018

(87) PCT Pub. No.: WO2017/214309
PCT Pub. Date: Dec. 14, 2017

(65) Prior Publication Data
US 2019/0333603 A1 Oct. 31, 2019

Related U.S. Application Data

(60) Provisional application No. 62/346,642, filed on Jun. 7, 2016.

(51) Int. Cl.
*G16B 25/00* (2019.01)

(52) U.S. Cl.
CPC .................................. *G16B 25/00* (2019.02)

(58) Field of Classification Search
CPC ..................................................... G16B 25/00
USPC ........................................................ 702/19
See application file for complete search history.

*Primary Examiner* — Jerry Lin
(74) *Attorney, Agent, or Firm* — Fletcher Yoder P.C.

(57) ABSTRACT

Embodiments of methods, systems, and tangible non-transitory computer readable medium having instructions are presented. A method includes calculating a plurality of feature values for a number of bioinformatic features of the desired hybridization reaction; and calculating distances between the plurality of feature values and corresponding database rate constant values stored in a database, the database comprising a plurality of hybridization reactions having known rate constants. The method additionally includes calculating a weighted average of a logarithm of the database rate constant values, with larger weights assigned to value instances having values lower in distance to the plurality of feature values of the desired hybridization reaction; and providing the weighted average as a predicted logarithm of the rate constant of the desired hybridization reaction.

25 Claims, 22 Drawing Sheets

Specification includes a Sequence Listing.

1100

FEATURE $Gb = \sum Pr(S_a) \Delta G°(S_a)$ $\Delta G°(S_1) = -45.28$    $Pr(S_1) = 0.289$ $S_1$ ACACACTGAAGGAGCTGTAGCATCCAAGAATACTAG
TGTGTGACTTCCTCGACATCGTAGGTTCTTATGATC $\Delta G°(S_4) = -44.58$    $Pr(S_4) = 0.093$ $S_2$ A CACACTGAAGGAGCTGTAGCATCCAAGAATACT AG
T GTGTGACTTCCTCGACATCGTAGGTTCTTATGA CT $\Delta G°(S_{10}) = -42.85$    $Pr(S_{10}) = 0.006$ $S_3$ ACACACTGAAGGAGCTGTAGCATCCAAGAA T ACTAG
TGTGTGACTTCCTCGACATCGTAGGTTCTT A TGATC

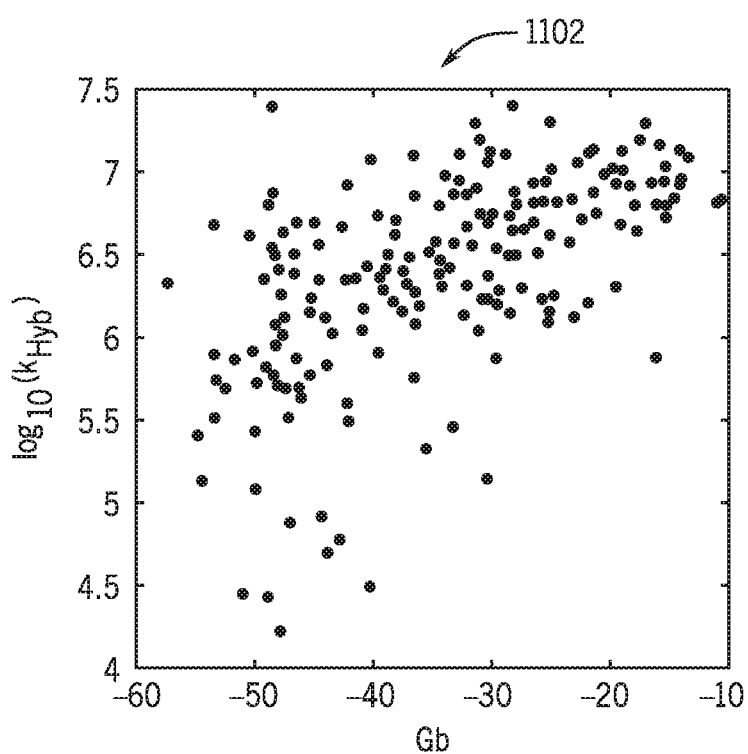

FIG. 11B

METHOD, APPARATUS, AND COMPUTER-READABLE MEDIUM FOR PREDICTING A HYBRIDIZATION RATE CONSTANT OF A FIRST SEQUENCE

CROSS REFERENCE TO RELATED APPLICATIONS

This application claims priority from and the benefit of U.S. Provisional Application Ser. No. 62/346,642, filed Jun. 7, 2016, entitled "METHOD, APPARATUS, AND COMPUTER-READABLE MEDIUM FOR PREDICTING A HYBRIDIZATION RATE CONSTANT OF A FIRST SEQUENCE," which is incorporated by reference in its entirety for all purposes.

STATEMENT OF GOVERNMENT INTEREST

This invention was made with U.S. government support under Grant Number ROIHG008752 awarded by the National Institutes of Health. The U.S. government has certain rights in the invention.

SEQUENCE LISTING

The instant application contains a Sequence Listing which has been filed electronically in ASCII format and is hereby incorporated by reference in its entirety. Said ASCII copy, created on Jul. 8, 2019, is named 2016-109-03_RICE0020_SL.txt and is 22,441 bytes in size.

BACKGROUND

Oligonucleotide probes and primers play a vital role in nucleic acid analytic and diagnostic chemistry and biotechnology. Assays such as fluorescent in situ hybridization, microarray expression analysis, and hybrid-capture enrichment for next-generation sequencing (NGS) are kinetically limited by the speed of probe hybridization. Rational selection of fast-binding target subsequences and design of fast-hybridizing probes can reduce hybridization time to enable faster assays, or alternatively reduce probe concentration needed and enable more highly multiplexed assays.

To date, the effects of target and probe sequences on the hybridization kinetics have not been systematically studied, and no predictive model or algorithm exists for predicting of hybridization rate constants from sequence and experiment conditions. It is known qualitatively that secondary structure in a target or probe sequence will interfere with and slow down hybridization. Consequently, typical probe design software will apply bioinformatics to select target and probe regions that are predicted to exhibit weak or no secondary structure at equilibrium in the hybridization conditions. However, biological nucleic acids often exhibit significant secondary structures in regions of interest, and empirical trial-and-error testing is often used to select probes to subsequences of these difficult regions.

BRIEF DESCRIPTION OF THE DRAWINGS

FIG. 10b illustrates two examples of fit quality for 3 reaction models shown in FIG. 10a;

FIG. 11a illustrates rate constant prediction using a Weighted Neighbor Voting (WNV) model, FIG. 11a discloses SEQ ID NOS 76, 76, and 76, respectively, in order of appearance;

FIG. 11b illustrates example relationship between the base-10 logarithm of the experimental hybridization rate constants kHyb (based on reaction model H3) vs. Gb values for the 210 hybridization experiments;

DETAILED DESCRIPTION

Figures 1A, 1B:
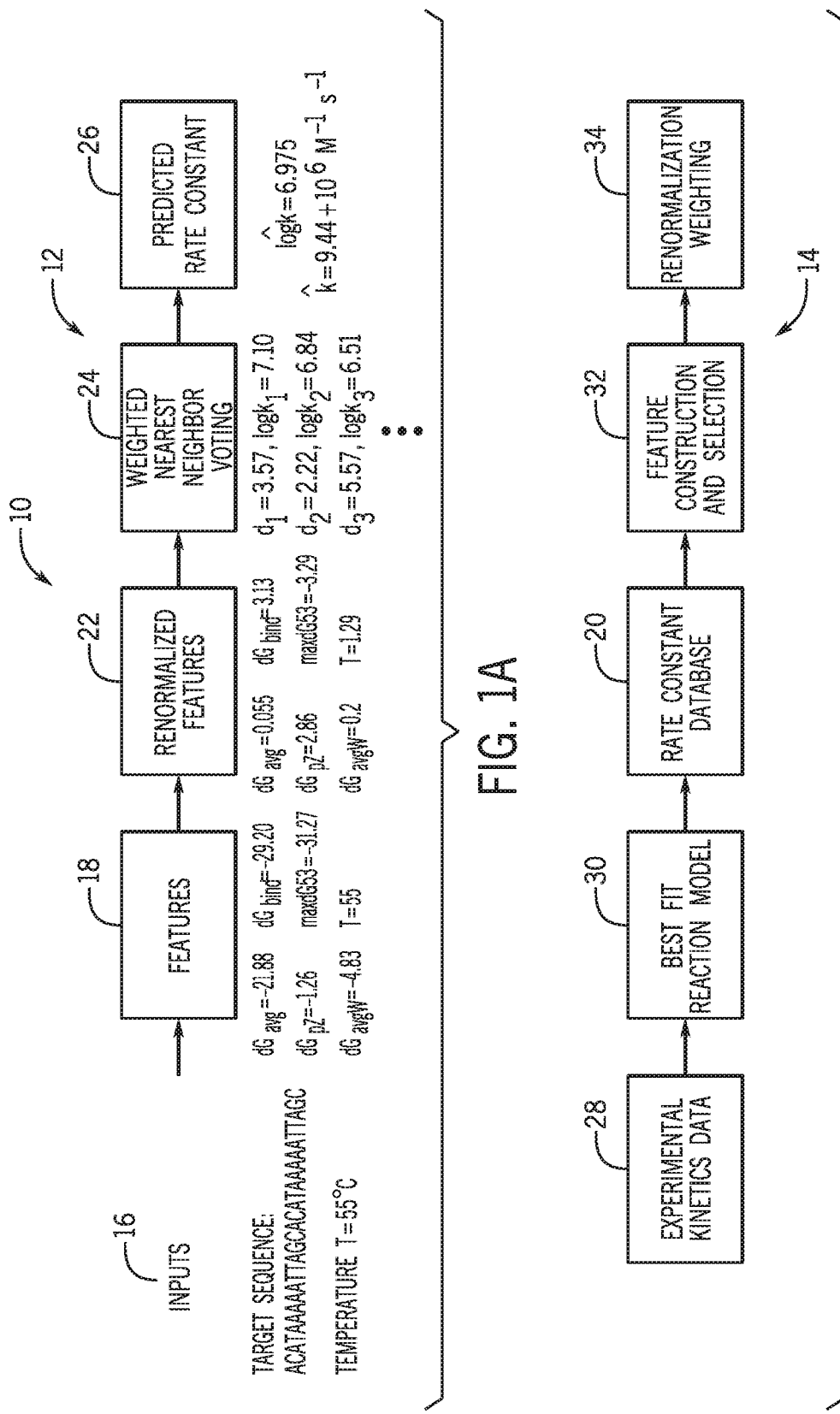
FIG. 1a illustrates an embodiment of a kinetics prediction workflow process suitable for deriving a predicted hybridization rate constant $k_{Hyb}$ for a user-defined target sequence, FIG. 1a discloses SEQ ID NO: 107.
FIG. 1b illustrates an embodiment of a process suitable for deriving hybridization rate constant prediction model(s) based on experimental kinetics data.

While methods, apparatuses, and computer-readable media are described herein by way of examples and embodiments, those skilled in the art recognize that methods, apparatuses, and computer-readable media for predicting a hybridization rate constant of a first sequence are not limited to the embodiments or drawings described. It should be understood that the drawings and description are not intended to be limited to the particular form disclosed. Rather, the intention is to cover all modifications, equivalents and alternatives falling within the spirit and scope of the appended claims. Any headings used herein are for organizational purposes only and are not meant to limit the scope of the description or the claims. As used herein, the word "may" is used in a permissive sense (i.e., meaning having the potential to) rather than the mandatory sense (i.e., meaning must). Similarly, the words "include," "including," and "includes" mean including, but not limited to. When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The techniques described herein include methods, systems, apparatuses, and computer-readable media for predicting, for example, a hybridization rate constant $k_{Hyb}$ of a sequence. The techniques include the steps of receiving a first sequence (such as a probe DNA sequence), calculating a set of feature values corresponding to one or more features of a hybridization reaction, wherein the set of feature values is calculated based at least in part on a hybridization reaction between the first sequence and a second sequence (such as a target sequence), determining one or more distances (such as Euclidean distances) between the set of feature values and one or more other sets of feature values corresponding to one or more other hybridization reactions, and calculating a predicted hybridization rate constant for the hybridization reaction between the first sequence and the second sequence based at least in part on the one or more distances and one or more other hybridization rate constants corresponding to the one or more other hybridization reactions.

The one or more features can include a temperature of the hybridization reaction. The one or more features can also be based on one or more of a calculated ensemble standard free energy of the first sequence, a calculated ensemble standard free energy of the second sequence, a calculated ensemble standard free energy of a duplex formed through hybridization of the first sequence and second sequence at predetermined temperature and buffer conditions, a calculated standard free energy of a minimum free energy structure (mfe) of the first sequence, a calculated standard free energy of a mfe of the second sequence, a calculated standard free energy of a mfe of a duplex formed through hybridization of the first sequence and second sequence at predetermined temperature and buffer conditions, a difference between a calculated ensemble standard free energy and a calculated standard free energy of a mfe of a duplex formed through hybridization of the first sequence and second sequence at predetermined temperature and buffer conditions, a calculated standard free energy of strongest-binding N nucleotide subsequence of the first sequence at predetermined temperature and buffer conditions, a calculated maximum probability of a N nucleotide subsequence of the first sequence being all in unpaired states at equilibrium, and/or a calculated maximum probability-weighted standard free energy of binding of a N nucleotide subsequence of the first sequence being in all in unpaired states at equilibrium.

Calculating a predicted hybridization rate constant for the hybridization reaction between the first sequence and the second sequence may be based at least in part on the one or more distances and one or more other hybridization rate constants corresponding to the one or more other hybridization reactions can include weighting each of the one or more other hybridization rate constants based at least in part on the one or more distances between the set of feature values and one or more other sets of feature values corresponding to one or more other hybridization reactions, calculating a weighted average of a logarithm of the one or more other hybridization rate constants, and transmitting the weighted average as a predicted logarithm of the hybridization rate constant for the hybridization reaction between the first sequence and the second sequence.

Additionally, the method can include normalizing the set of feature values prior to determining one or more distances. In this case, determining one or more distances between the set of feature values and one or more other sets of feature values corresponding to one or more other hybridization reactions can include determining one or more distances between the normalized set of feature values and one or more other sets of normalized feature values corresponding to one or more other hybridization reactions.

Turning now to FIGS. 1a and 1b, the techniques described herein include a novel Weighted Nearest Neighbor (WNN) process 10 suitable for predicting hybridization kinetics based on target sequence and experimental conditions. The WNN process 10 may include a hybridization rate constant prediction process 12 shown in FIG. 1a, and a model building process 14 suitable for constructing a hybridization rate constant model. In one embodiment of the WNN process 10, each hybridization reaction, comprising a target sequence 16, a probe sequence, and a set of hybridization conditions (e.g., temperature, buffer), may be represented by a set of bioinformatic features 18 that are constructed. Two hybridization reactions with similar feature values (e.g., having a smaller distance in feature space) are expected to be more likely to exhibit similar hybridization kinetics. A desired hybridization reaction's features 18 is compared with a database of known hybridization reactions 20, and each instance of the database 20 makes a "vote" for the predicted rate constant, with smaller vote weights for more dissimilar instances.

To quantify the similarity or dissimilarity between two hybridization reactions, each reaction can be abstracted into a number of bioinformatic features 18. The value of each feature 18 for a particular hybridization reaction is computable based at least in part on one or more of the sequence of the target 16, the sequence of the probe, the reaction temperature, and/or buffer conditions. Each hybridization reaction is thus a point in feature space. With an optimally designed set of features 18, the two points close in feature space (small Euclidean distance) should exhibit similar values of $k_{Hyb}$, the second order rate constant of hybridization. The converse is not necessarily true, two hybridization reactions with coincidentally similar $k_{Hyb}$ values may possess very different feature values.

Mapping the hybridization reactions into feature space may be important because targets that are similar in sequence space may not be similar in hybridization kinetics, and vice versa, due to the sensitivity of secondary structure to small changes in DNA sequence in certain regions, but not in others.

For example, oligonucleotide (2) with sequence "ACACACACAAAAAAAAGTGTGTGT" (SEQ ID NO: 101) has higher Hamming distance to oligonucleotide (1) with sequence "ACACACACTTTTTTTTGTGTGTGT" (SEQ ID NO: 102) than oligonucleotide (3) with sequence "AGTCAGACTTTTTTTTGTGTGTGT" (SEQ ID NO: 103), but is expected to exhibit much more similar kinetics in hybridization to each's respective complement. In this case, one possible feature 18 can be the number of base pairs formed in the stem of any hairpins in the minimum free energy structure of the oligonucleotide: oligonucleotide (1) and (2) would have feature value 8, while oligonucleotide (3) has feature value 6.

As shown in FIG. 1a, the hybridization rate constant prediction process 12 may take us the target sequence 16 as input. In the depicted embodiment, the features 18 include six bioinformatics features such as Temperature (T), dGavg, dGbind, dGpZ, maxdG53, and dGavgW. One set of example values is shown in the figure for each of the six features 18, which may be computed as described in more detail below, for example, with respect to FIGS. 2-3. The hybridization rate constant prediction process 12 may then renormalize the features 18 resulting in renormalized features 22 as described in more detail below, for example, with respect to FIG. 4. The process 12 may then apply a weighed neighbor voting 24, with weight decreasing based on distance to the target 16 in feature 18 space. The weighed neighbor voting 24 then may result in the derivation of a predicted rate constant, such as $k_{Hyb}$. It is to be understood that while the techniques described herein are described with respect to DNA and/or RNA, the techniques may alternatively or additionally be used for protein structures, such as amino acid sequences, ensembles, and the like.

The process 14 suitable for creating hybridization rate constant prediction model(s) may apply experimental kinetics data 28, such as reaction data, to one or more best fit reaction model(s) 30. The model(s) 30 may access the rate constant database 20 for feature construction and selection 32. As mentioned above, the features 18 as constructed and selected (block 32) via the model 30 and database 20 may then be renormalized and weighed (block 34) to derive the predicted rate constant 26. In this manner, hybridization rate constants from sequence and reaction conditions (e.g., temperature, buffer, salinity) may be provided, useful for a variety of biomedical applications.

Figure 2A:
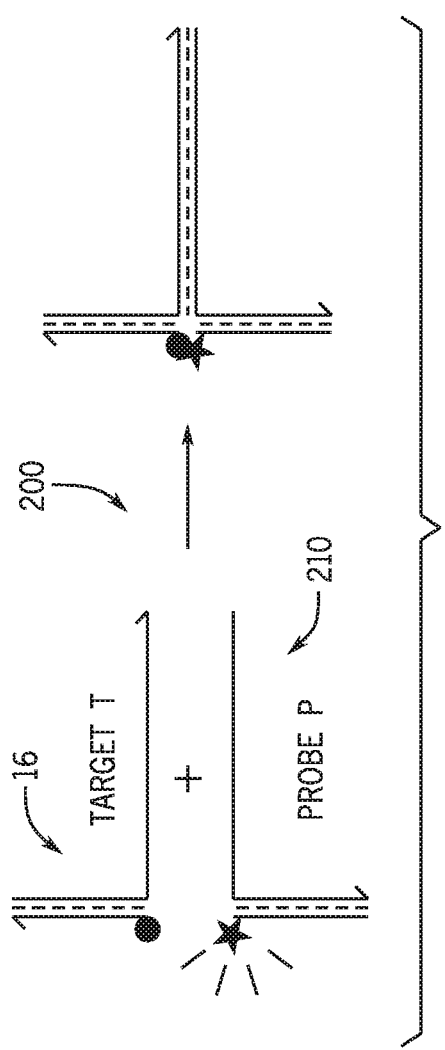
FIG. 2a illustrates an embodiment of fluorescent probes with universal functionalized oligonucleotides.
Figure 2B:
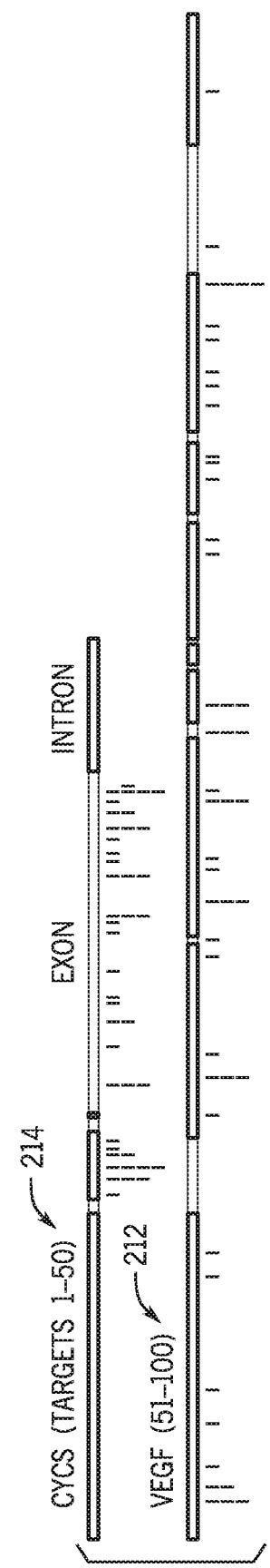
FIG. 2b shows embodiments of 100 different subsequences of the CYCS and VEGF genes that were selected to the target sequences.

Experimental Data:

Turning now to FIGS. 2a-d, the figures shows an example experimental setup and data 28 used for training a WNN model, such as model 30. 210 different hybridization experiments, such as an experiment labeled 200, were performed on 100 different pairs of target 16 and probe sequences 210 (e.g., fluorescent probes), as shown in FIG. 2a. Fluorescence is initially high, and decreases as the hybridization reaction proceeds because the fluorophore (star) becomes localized to the quencher (dot). Each hybridization reaction was monitored in real time using fluorescence, and the rate constant $k_{Hyb}$ was fitted to the kinetics traces. The target sequences 16 were selected as subsequences of the VEGF and CYCS genes, 212, 214, respectively, as shown in FIG. 2b. For this study, all target and probe sequences are 36 nt long (excluding universal regions). 25 targets for each gene were chosen randomly with uniform distribution across the entire intron and exon region, and the other 25 targets were selected as close overlapping frames to systematically test the position effects of secondary structures.

Figure 2C:
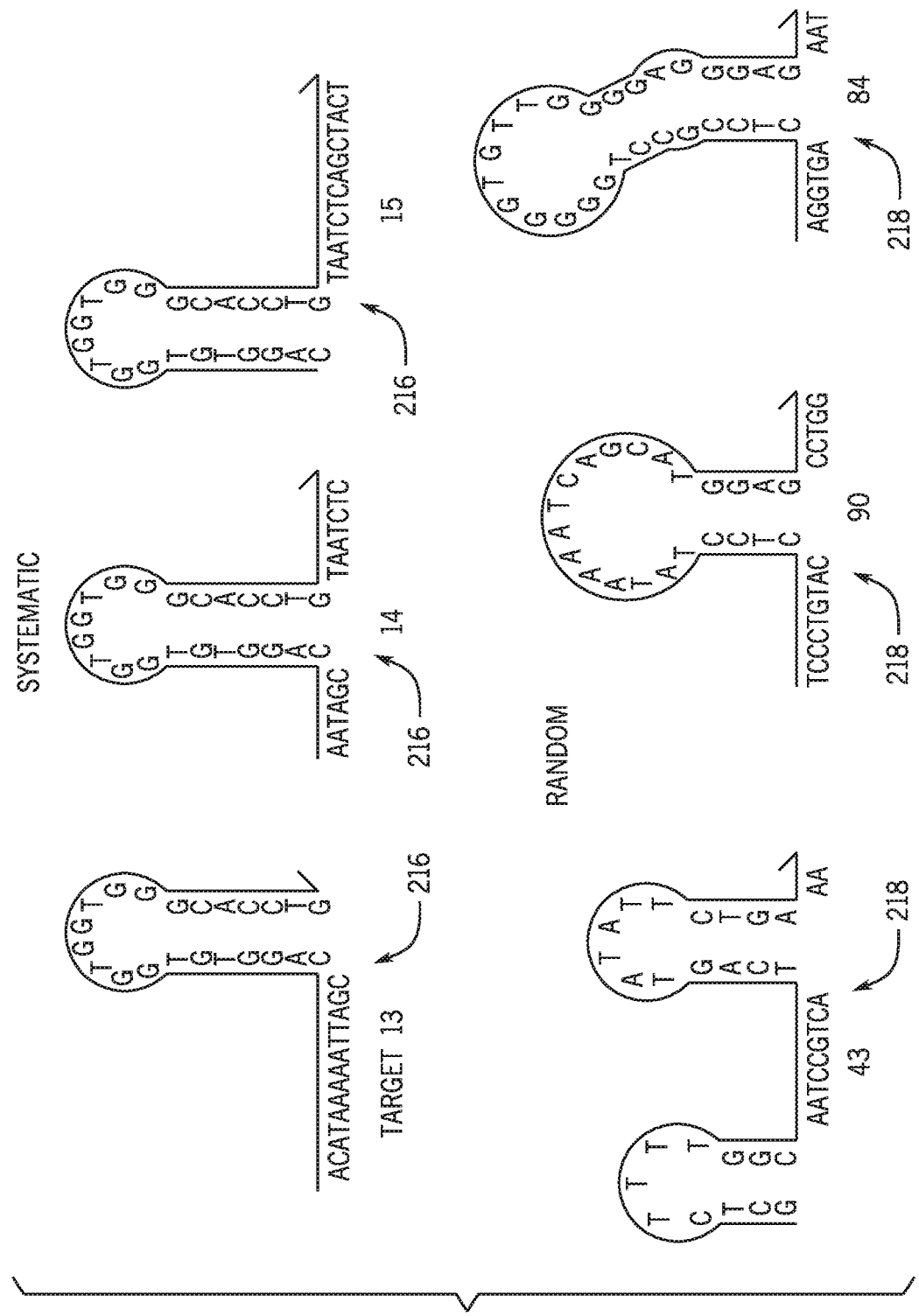
FIG. 2c depicts examples of secondary structures encountered in target sequences, FIG. 2c discloses SEQ ID NOS 13, 108, 15, 43, 90, and 109, respectively, in order of appearance.
Figure 2D:
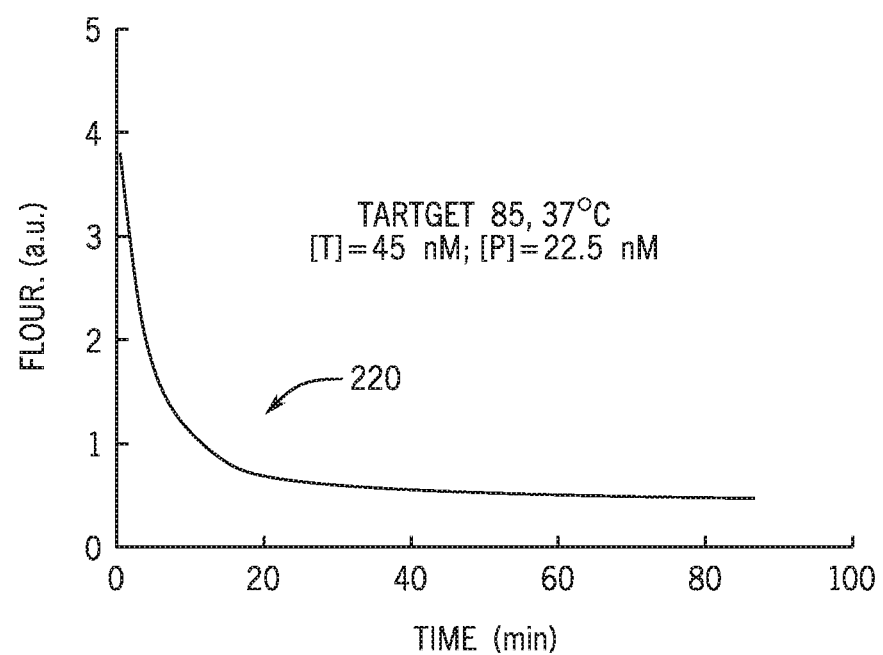
FIG. 2d illustrates example kinetic traces (triplicate) of a hybridization reaction.

FIG. 2c illustrates example secondary structures encountered in target sequences, including systematic structures 216 and random structures 218. Shown are predicted minimum free energy (mfe) structures predicted for the target sequences at 37° C. FIG. 2d depicts example kinetic traces 220 for a hybridization reaction test, showing decay over time at 37° C. All reactions proceeded in 5×PBS buffer.

Bioinformatic Features:

From an initial candidate pool of over 40 bioinformatic features, the feature list was pruned to remove features that did not contribute significantly to the prediction of hybridization rate constant kHyb, either because they did not significantly impact kHyb or because their effects were redundantly captured by other features. The final WNN modeling uses 6 features 18: Temperature, dGavg, dGbind, dGpZ, maxdG53, and dGavgW. Temperature is simply the temperature of the hybridization reaction, in Celsius.

dGbind is the standard free energy of hybridization of the target subsequence and the probe, at the hybridization reaction conditions. Its value can be calculated from nucleic acid thermodynamics prediction parameters, by summing the standard free energies of each base stack. Its value can also be calculated via thermodynamics prediction tools such as Nupack and mFold, e.g. via the "mfe" function.

dGavg=$\Sigma Pr\_ij*dG\_ij$, over all $1 \leq i < j \leq N$, where N is the length of the target subsequence, corresponds to the standard free energy of hybridization a subsequence from nucleotides i through j to its exact complement (dG_ij), weighted by the probability of all nucleotides from i through j being in an unbound state in single-stranded form (Pr_ij). Pr_ij can be calculated as the product of Pr_k, with k ranging from i through j. Pr_k can be calculated using nucleic acid thermodynamics prediction tools such as Nupack, e.g. via the "pairs" function. dG_ij can be calculated using nucleic acid thermodynamics prediction parameters as in dGbind, counting only the base stacks from nucleotides i through j.

dGavgW=$(\Sigma Pr\_ij*dG\_ij)/(\Sigma Pr\_ij)$ is calculated similarly to dGavg, but is weighted by the total sum of the probabilities of all subsequences being in unbound states.

dGpZ is the partition function energy of folding of the single-stranded probe oligonucleotide, and can be calculated using nucleic acid thermodynamics prediction tools such as Nupack, e.g. via the "pfunc" function.

maxdG53 is calculated as the stronger (more negative) standard free energy of binding of the 5'-most and 3'-most unpaired nucleotides of the target in its single-stranded minimum free energy state. In standard dot-parenthesis notation, the standard free energy of binding of the first i nucleotides that are unpaired (dots) and the last j nucleotides that are unpaired are both evaluated, and maxdG53 is set as the more negative value.

Figure 3:
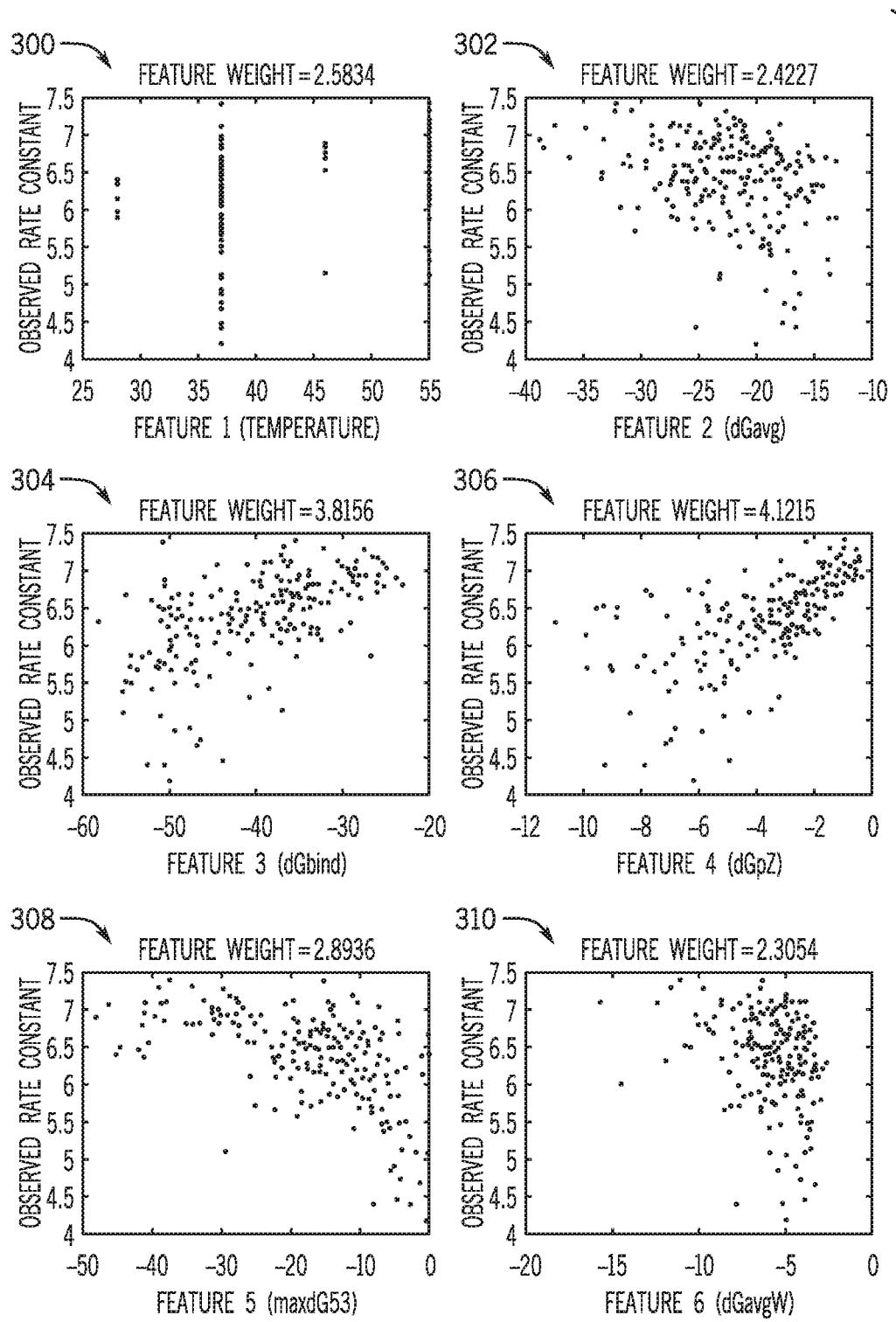
FIG. 3 illustrates correlation of individual features with hybridization rate constant $k_{Hyb}$.

FIG. 3 shows the rate constants kHyb plotted against each of six feature 18 example values. More specifically, six graphs 302, 304, 306, 308, 310, and 312 are shown, based on Temperature, dGavg, dGbind, dGpZ, maxdG53, and dGavgW, respectively. Each of the graphs 302-312 includes an x-axis having feature values and a y-axis having an observed rate constant. Each of the graphs 302-312 also includes a feature weight for each of the six features 18. A correlation indicates that these feature values may be effective for rate constant prediction. The calculated feature values for all hybridization reactions (temperature and sequence) are listed later in this document under the heading "Sequences, Feature Values, and Observed Rate Constants".

Figure 4:
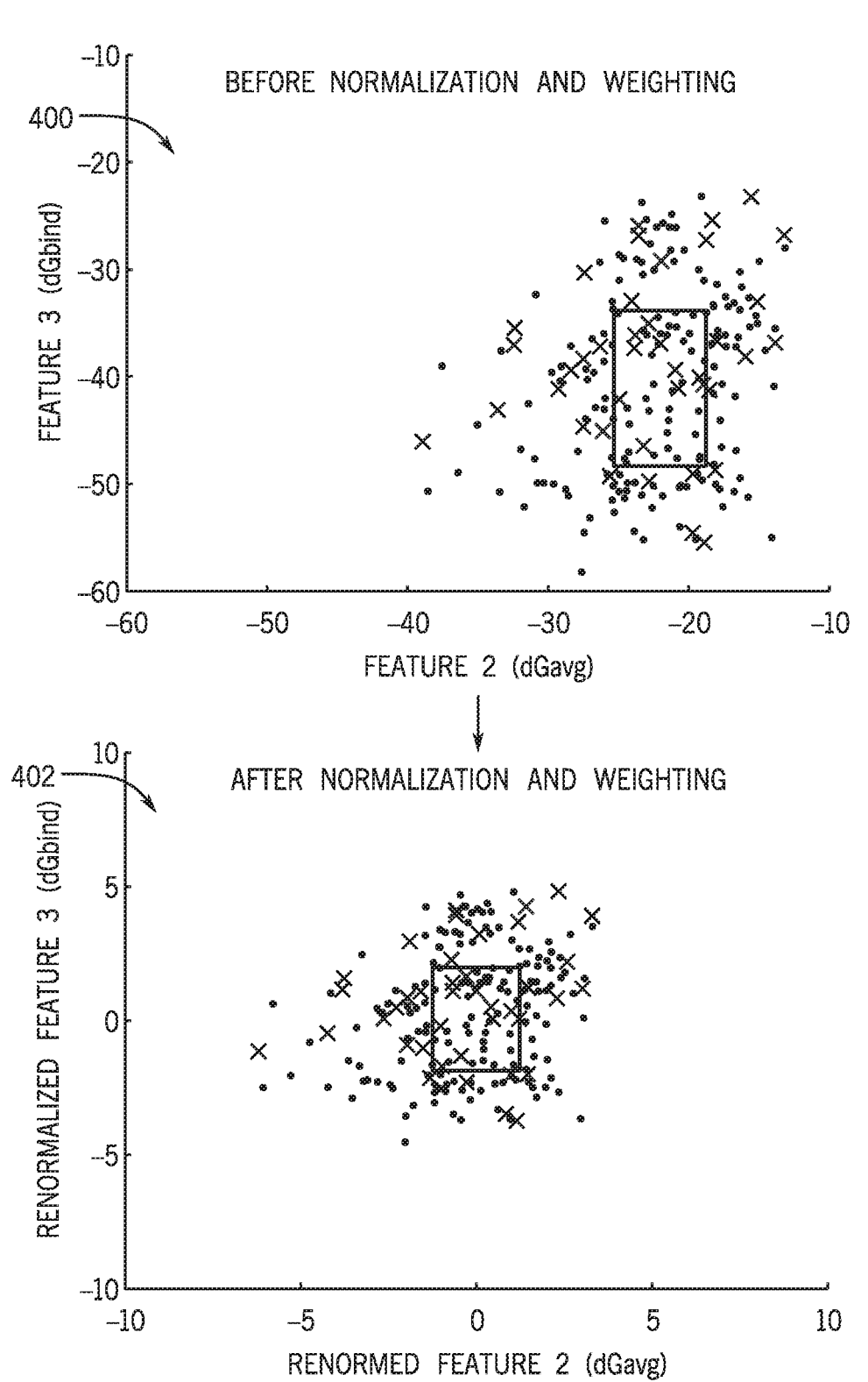
FIG. 4 illustrates feature renormalization. (c) Scatter plot of values for features 2 and 3 (dGavg and dGbind)

Feature Renormalization:

The constructed features can have different units and different ranges of values. In order to accurately calculate a Euclidean distance between two hybridization reactions, the different features can be normalized. Because the distributions of most feature values may be distinctively non-Gaussian, normalization can be performed based on the interquartile range. Turning now to FIG. 4, the figure depicts graphs 400 and 402 suitable for illustrating before and after normalization and weighing of features 18. More specifically, graph 400 depicts dGavg in the x-axis and dGbind in the y-axis before normalization and weighing.

In normalized and weighed graph 402, the 75th percentile feature value is mapped to a score of +w/2, and the 25th percentile value is mapped to −w/2. Different features can be assigned different weights w, to indicate their importance in prediction of the rate constant $k_{Hyb}$. A feature with larger weight w allows a larger range of scores, and can contribute more to the overall distance. The data set was divided into a training set (80% of experiments, dots) and a test set (20%, X's); the depicted box indicates the 25th to 75th percentile ranges of the training set for each feature. Renormalization of feature values. The 75th percentile value of feature j is renormalized to +wj/2 and the 25th percentile value is renormalized to −wj/2. All other feature values are linearly transformed based on these reference values. Optimal weights wj were determined through numerical optimization.

Figure 5:
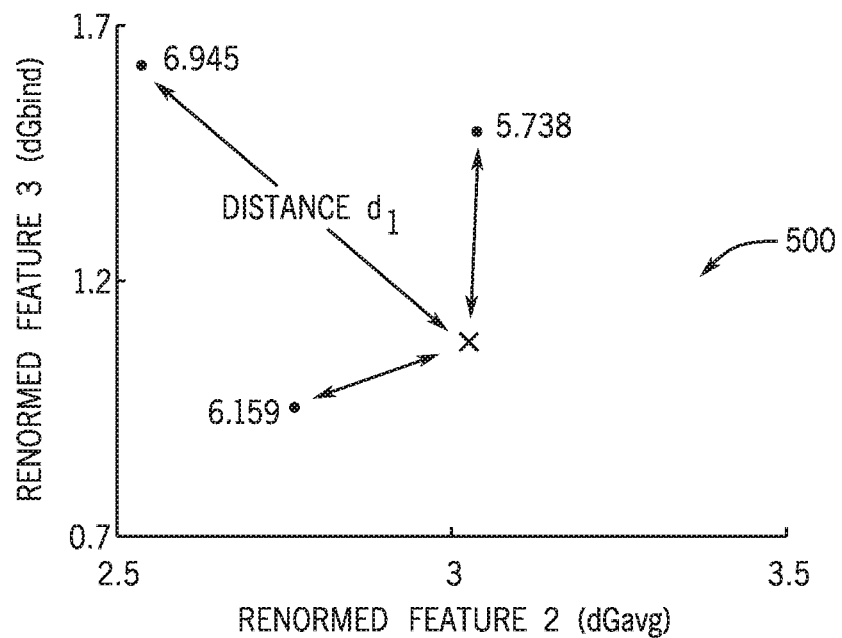
FIG. 5 illustrates example distance calculation and rate constant prediction.

Distance Calculation and Rate Constant Prediction:

From a database of hybridization experiments that pairs normalized feature values with $k_{Hyb}$, such as database 20, a prediction for $k_{Hyb}$ of a new hybridization reaction can be made as shown in FIG. 5. The Euclidean distance between a target sequence's features (X) and each training instance's features is computed and used to determine the weight of the training instance's vote. Displayed numbers are the log (base 10) of the observed experimental rate constants for the training instances, which are integrated to predict the log of the hybridization rate constant of the target sequence. Farther training instances contribute exponentially less to the overall prediction. The formula used for prediction can be:

$$log \hat{k} = \frac{1}{Z} \Sigma_i log k(i) e^{-d_i/D}$$

where log k(i) is the logarithm (base 10) of the ith database entry, $d_i$ is the distance, e.g., $d_i = \sqrt{(f_j(target) - f_j(i))^2}$, D is a distance constant (arbitrarily set as 5), and $Z = \Sigma_i e^{-d_i/D}$ is the "partition function" of the distance. Thus, in this model, the weight of a database entry i drops off exponentially with distance. The value of distance constant D does not have significant impact on the performance of the WNN model, as the same $k_{Hyb}$ predictions can be achieved by scaling the feature weights w with D.

The six features described earlier (Temperature, dGavg, dGbind, dGpZ, maxdG53, and dGavgW) have final weights of 2.58, 2.42, 3.82, 4.12, 2.89, and 2.31, respectively, under the assumption of D=5. Using this set of feature weights maximizes the prediction accuracy of the model on our current dataset.

Figure 6:
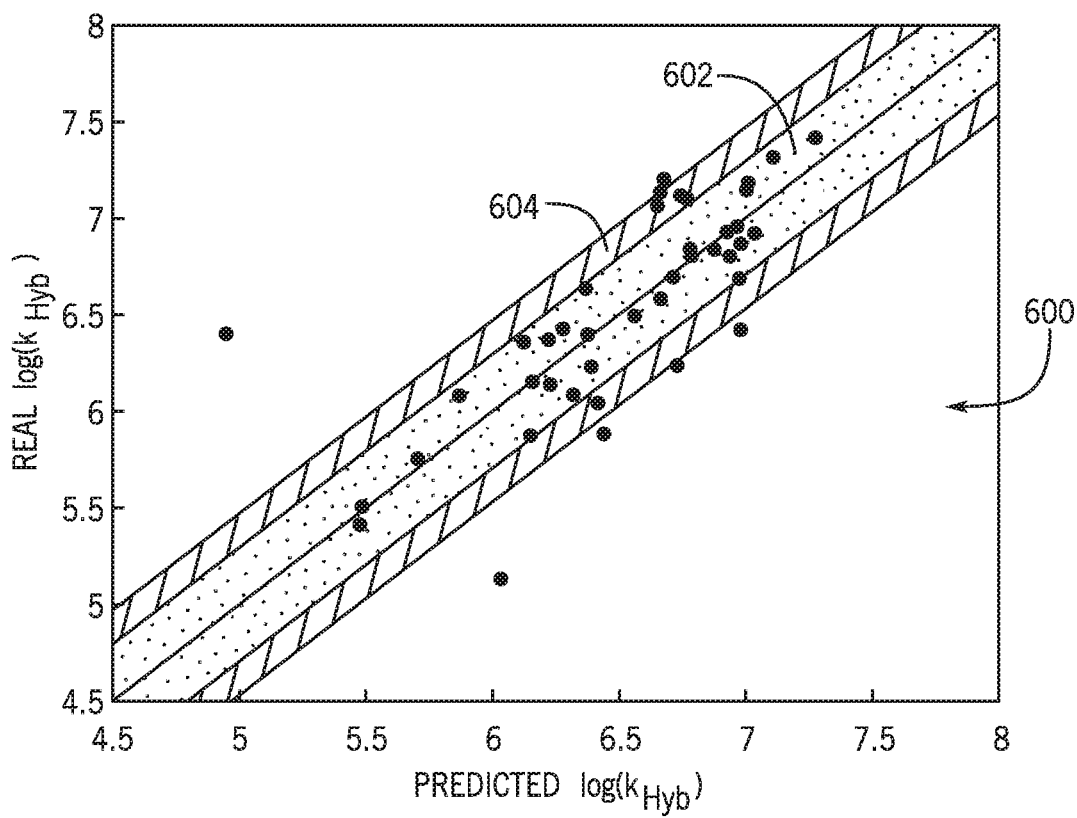
FIG. 6 illustrates an example performance of an embodiment of a WNN model, based on a particular partition of the experimental dataset into training and test sets.
Figure 7:
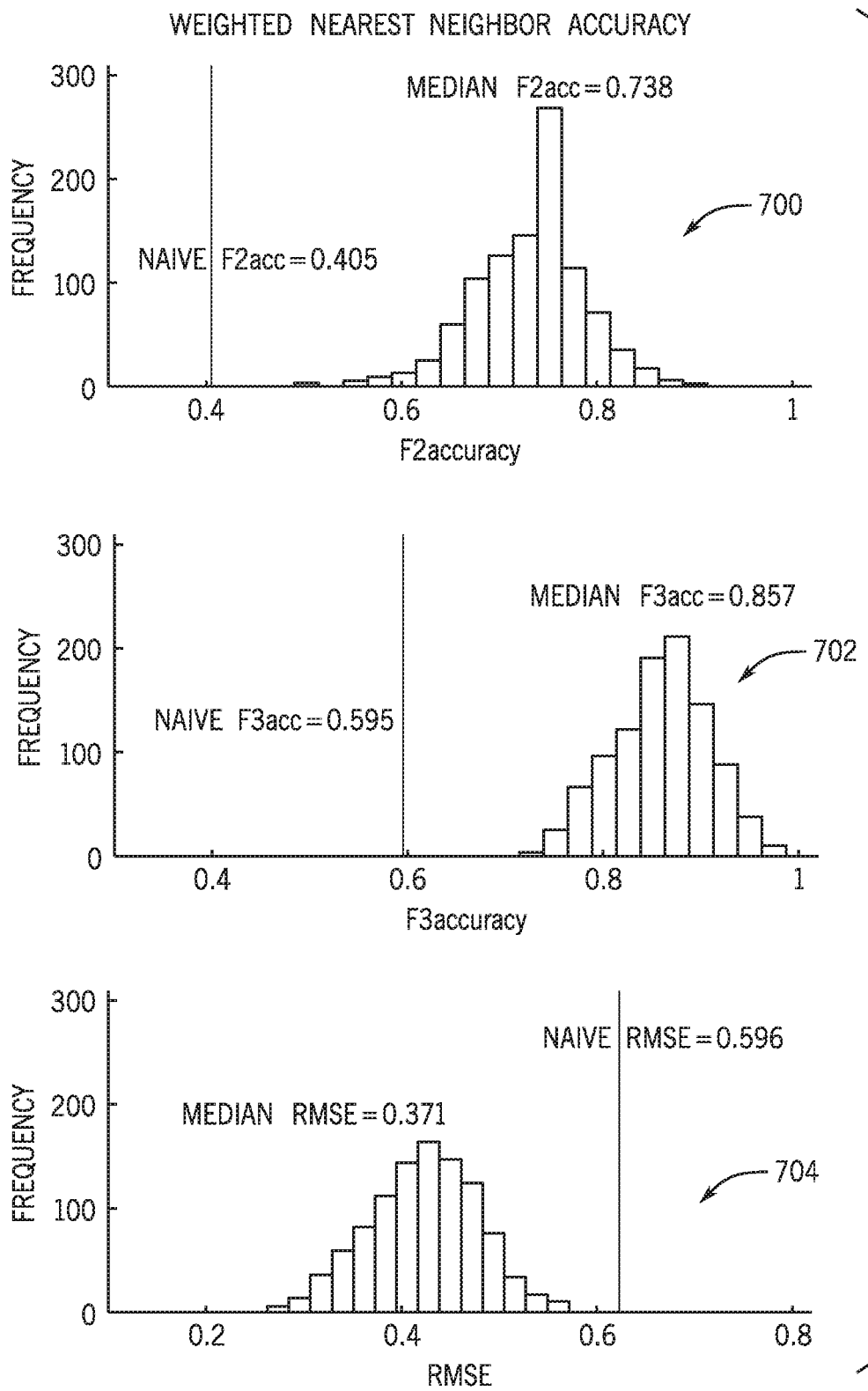
FIG. 7 illustrates statistics on WNN model rate constant prediction performance, across 1000 partitions of dataset into training and test sets.

Cross-Validation and Prediction Accuracy:

FIG. 6 illustrates prediction accuracy of an embodiment of the final WNN model for one particular partition of the dataset into training and test sets. For example, graph 600 of FIG. 6 shows real versus predicted data in axes y and x, respectively. A darker shaded region 602 indicates correctness to within a factor of 2, and a lighter shaded region 604 indicates correctness to within a factor of 3. FIG. 7 shows the statistics for 1000 different partitions of the data into training and test sets. The median performance of the WNN model was 73.8% accuracy to within a factor of 2 (F2accuracy) shown in graph 700, 85.7% to within a factor of 3 (F3accuracy) shown in graph 702, and 0.371 root mean square error (RMSE) shown in graph 704. These represent marked improvement over the naive model in which all training data were weighted equally. Different training and test set partitions result in variation in prediction performance, because some partitions result in regions in feature space that are sparsely represented, resulting in larger distances and less accurate prediction.

Figure 8:
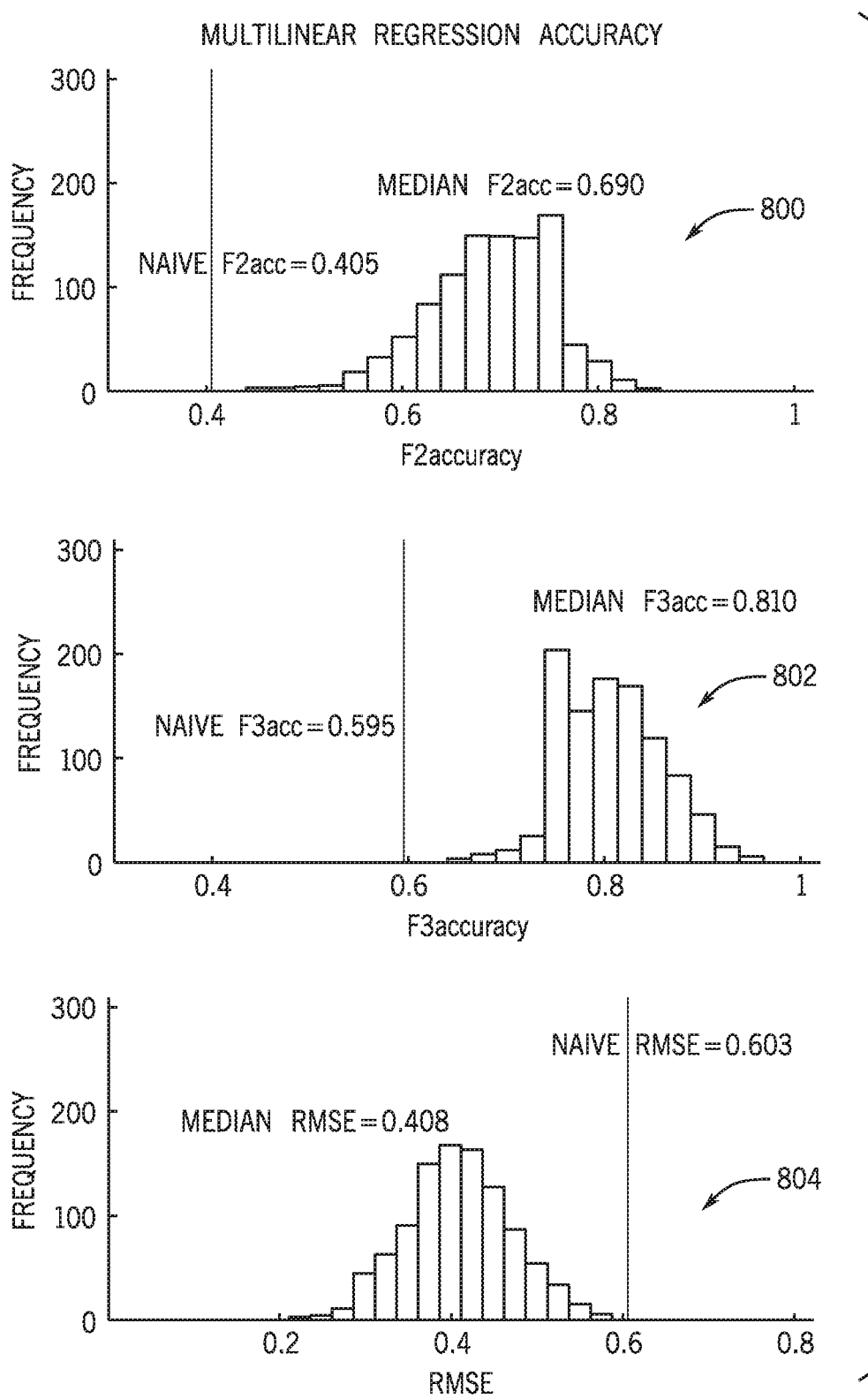
FIG. 8 illustrates statistics on multilinear regression model performance, as comparison.

Another approach to rate constant prediction is a multilinear regression based on the constructed features as shown in FIG. 8. Using the same approach of testing on 1000 different partitions of the dataset, the best-performing 6-feature 18 multilinear regression provided median F2accuracy=69.0% shown in graph 800, F3accuracy=81.0% shown in graph 802, and RMSE=0.408 shown in graph 804. It is believed that the WNN model performs better than the multilinear regression approach because the latter approach over-weighs the information from hybridization experiments highly dissimilar to the reaction of interest. Indeed, performance is inferior to WNN model on all three metrics.

Additional Enhancements:

Based on biophysical knowledge of the hybridization process, over 30 features were constructed that are believed to be correlated to the hybridization rate constant kHyb; these were pruned down to 6 final features without reduction of prediction accuracy. The high cross-validation accuracy of the WNN model indicates that these features capture a significant, if not majority, portion of the complexity of the hybridization process. Simultaneously, there remain pairs of experiments in our database with similar feature values (distances≤1) but with a 10-fold difference in kHyb. This implies that there are features that distinguish these experiments and these additional features can also be incorporated into the WNN model.

The WNN model is highly scalable to the addition of new experimental data, as the underlying weights and features are not changed. This is an advantage over multilinear regression-based approaches, in which new data necessitates new regression coefficients. With every additional hybridization experiment and its accompanying fitted kHyb value, the 6dimensional feature space becomes denser, ensuring that on average a new hybridization experiment will be closer to an existing instance.

Sequences, Feature Values, and Observed Rate Constants:
A listing of 100 sequences is presented in the table below:

| SEQ ID NO: | |
|---|---|
| 1 | AAGATGGTGAGTGCCATCTTAAAACTTACTGGAGAT |
| 2 | TTTTCACAAAGATGGTGAGTGCCATCTTAAAACTTA |
| 3 | TGTTCAACTTTTCACAAAGATGGTGAGTGCCATCTT |
| 4 | TTCCCTCCTGGAAAGCCGAAGCTTAGAGCTTCACGT |
| 5 | ACTTCCCTCCTGGAAAGCCGAAGCTTAGAGCTTCAC |
| 6 | AGACTTCCCTCCTGGAAAGCCGAAGCTTAGAGCTTC |
| 7 | TGGGATGTCCCCGGGGACCGTGCAGCCTGCCCCTG |
| 8 | GTTGGGATGTCCCCGGGGACCGTGCAGCCTGCCCC |
| 9 | GGAGTTGGGATGTCCCCGGGGACCGTGCAGCCTGC |
| 10 | CAGGCGTGAGCCACCACGCCTGGCCAATTATGTAAT |
| 11 | GGGATTACAGGCGTGAGCCACCACGCCTGGCCAATT |
| 12 | AAGTGCTGGGATTACAGGCGTGAGCCACCACGCCTG |
| 13 | ACATAAAAATTAGCCAGGTGTGGTGGTGGGCACCTG |
| 14 | AATTAGCCAGGTGTGGTGGTGGGCACCTGTAATCTC |
| 15 | CAGGTGTGGTGGTGGGCACCTGTAATCTCAGCTACT |
| 16 | TTGGGAGGCCAAGGCAGGCAGATCACCTGAGGTCAG |
| 17 | ACTTTGGGAGGCCAAGGCAGGCAGATCACCTGAGGT |
| 18 | AGCACTTTGGGAGGCCAAGGCAGGCAGATCACCTGA |
| 19 | ACATTTAGAGTAGTCCTTGGAGATTTTATGGAGATG |
| 20 | AAGTTGCGGTTGTGGTGATTTTGGCTTAATGTGTTC |
| 21 | TCACAAGACTAAAGATAATTAAAAAGAAAACCACAG |
| 22 | GAAACCCCATCTCTACCAAAAATATAAAAACTAGCT |
| 23 | CTTAGTTGGAGTTTGGGGTATTTGAAAACGTCATGC |
| 24 | TCTGGTGGGAATTTAAAAATGCATCCTGGAAATCC |
| 25 | CTTGGAGATTTTATGGAGATGGTGAGCACAAGGTAA |
| 26 | GCACTTCTCTTGAATTCCTTTATAGATGTACAGTTT |
| 27 | ACAATAGTGAAACTCCGTCTCAAAAAGAAAAAAAGT |
| 28 | AAGATTAAATGGTTAGGTCTTTTTAAAAGTTGCGGT |
| 29 | AAATATTCATTCATGAGCTCTTTTGGCAATCCGTCA |
| 30 | TTTTATTTTTATTTTTTGAGATAATTTCACTCTTG |
| 31 | GGTCGCCCCAGGAGATCACAGGTAGGGGAGTTGGGA |
| 32 | CTCCAATTCAGTAAATGGTATCACTGTTTACCCCTT |
| 33 | ATCCGTCCACTTGCCTTGGCTCCCCAAAGTGCTGGG |
| 34 | AGGTTATCTTAGTTGGAGTTTGGGGTATTTGAAAAC |
| 35 | GCTATCATTTCCCTCAGAAAGCTAAGTAAATTTACT |
| 36 | AAATGTTTTGGTATTAAAGAATATTTGGTATAAAG |
| 37 | ATTCATTTCTCAAAGAGTAAAAGTGCAGGTTGTATG |
| 38 | CCAGGTTATCTTAGTTGGAGTTTGGGGTATTTGAAA |
| 39 | TATTCAGGGACAGTGTAGCAAGTAGCTTACAAGGGG |
| 40 | AATTTTACCATAAGTTTTACCTATTCGTAAGTTGGC |
| 41 | TGTCTCTTCTGAAACTGGAGTTTGAATTAGGTTCCC |
| 42 | TATAATTACATACTGAATTATTTCATGCATAGTCTG |
| 43 | GCTCTTTTGGCAATCCGTCATCAGTATATTCTGAAA |
| 44 | TACATTATATTGCCCTTCAGAATAGATTCCAGTTCC |
| 45 | TGGAGTTTGGGGTATTTGAAAACGTCATGCCTTCAG |
| 46 | GCCCAGCTTATTTTGTGTTTTTAGTAGAGACAGGGT |
| 47 | CCAAGCGGGGAGCATTCGAGTGGAGCCCGCGCTGGG |
| 48 | AGGAGGACTGCTTGTGCCCAGAAGTTCGAGGCTGCA |
| 49 | AACTTTGTCTCCCACATAAGTCTCTTCTAGGCACTG |
| 50 | TTTTAAAAAGGACATTTCTATCAGGGATATATACCT |
| 51 | CTGGGGCTGTTCTCATACTGGGGCTTTCTGCCCCAG |
| 52 | GTTCTCATACTGGGGCTTTCTGCCCCAGGACCACAC |
| 53 | CTGGGGCTTTCTGCCCCAGGACCACACCTTCCTGTC |
| 54 | GCTCCAGTGCACCCCAGGCTTCGTGGCCAGCCTGGG |
| 55 | GTGCACCCCAGGCTTCGTGGCCAGCCTGGGAAACTG |
| 56 | CCCAGGCTTCGTGGCCAGCCTGGGAAACTGTCTCTA |
| 57 | CTGTGAACTTCCCTCCCAGGCCAGCAGAGGGCTGGC |
| 58 | CCCTCCCAGGCCAGCAGAGGGCTGGCTGTAGCTCCC |
| 59 | GCCAGCAGAGGGCTGGCTGTAGCTCCCAGGCGCCCC |
| 60 | GTGTCAGGAGCCCCTCTCTCCCTCTCTTGGAGAGAG |
| 61 | GAGCCCTCTCTCCCTCTCTTGGAGAGAGTCCTGAG |
| 62 | CTCTCTCCCTCTCTTGGAGAGAGTCCTGAGTGCCCC |
| 63 | CCCTGTCACCCCGCTTATTTTCATTTCTCTCTGCGG |
| 64 | TCACCCCGCTTATTTTCATTTCTCTCTGCGGAGAAG |
| 65 | CCGCTTATTTTCATTTCTCTCTGCGGAGAAGATCCA |
| 66 | GCCATCCAATCGAGACCCTGGTGGACATCTTCCAGG |
| 67 | ATCGAGACCCTGGTGGACATCTTCCAGGAGTACCCT |
| 68 | CCTGGTGGACATCTTCCAGGAGTACCCTGATGAGAT |
| 69 | TTTATATATATATATATTATATATATATAAAAATAA |
| 70 | TTCCATACCTTCACAACACTTGTGCCTCCCCCAGGG |
| 71 | TACCTTCACAACACTTGTGCCTCCCCCAGGGCCTCT |
| 72 | CACAACACTTGTGCCTCCCCCAGGGCCTCTTTCTCA |
| 73 | CCCTGTACTTTCCACTGCCCTACCTAGATGTCCCTG |
| 74 | GAGATTTTGTCCCTTCATCCACCGGCTTCTAGATTA |

| SEQ ID NO: | |
|---|---|
| 75 | GGACTTGACATTTTAGGGTTTTTAGGTGATTATTCT |
| 76 | ACACACTGAAGGAGCTGTAGCATCCAAGAATACTAG |
| 77 | TGTCAACAAAGCACAGATGCTCTCGCTGGGGCCTTG |
| 78 | TCTGTCCTCAGTGGTCCCAGGCTGCACCCATGGCAG |
| 79 | ACCCAGTCTCGGCTTCCCACCAAAGCCTTGTCAGGG |
| 80 | AGCTGCCTCCCCCTTTGGGTTTTGCCAGACTCCACA |
| 81 | GCTCCGATGGGGCAACAGCAGTTGGGTCCCTGTGG |
| 82 | AATGTGACTTGGGTCCATTTGAATCCAAAGTCCCTG |
| 83 | GGCCGCTGGTCCCGGACGAACTGGAAGTCTGAGCAG |
| 84 | AGGTGAGCATGCCTGGGGGTGTTGGGGAGATGCAAT |
| 85 | TAAGTGAAGTCAAGTTGTTCAGGGGGCTAAGCCCAT |
| 86 | GAGGGCAGGGCTGGGGCTGTTCTCATACTGGGGCTT |
| 87 | AGCCCCTATTCCGGCCCAACCCATGGCACCCACAG |
| 88 | GCCAGCCTTGCACACACTTTGTCCTGGTGAAAGGCA |
| 89 | CTATAAATCCATGAGCAGAAAAATACATAAAATGTG |
| 90 | TCCCTGTACCTCCTATAAAATCAGCATGGAGCCTGG |
| 91 | CCAGGCAGTGGAGGCCAGCCCTCCTTGGAGGGGCGG |
| 92 | CCTGCATTTCGAGCTCCCCAGCCCCCAACATCTGGT |
| 93 | TACCTTTGTGAGCCCCGGGCATCTGTACCTCTTTCC |
| 94 | TCCGTTTCGGGGCTCCCCAGAAGGGTAGGGCCTGTT |
| 95 | GAGCAAACTCCCCCCACCCCCTTTCCAAAGCCCATT |
| 96 | AGTTTGCCCTCTTGGGCGGGGTTATCAGTGGCTGGC |
| 97 | ACCCCTTGCCCAGGCCAGACCTTCCTGCTATCCCCT |
| 98 | GCCTGATACACAGCCCTCCCTCCCACTCCTGCTCCC |
| 99 | CTTATGGCAGCCTCTCCCTGCACTCTCTGCCCGTCT |
| 100 | TCTCCCTCCTCAGACTGGGGCTCTGAGGGCAAGGGG |

The calculated values of each of the six previously identified features for these 100 sequences is listed in the table below:

| Sequence | k_Hyb | T | dG_average | binding Dg | pfprobe | max(5'/ 3' free) | Dg_average_2 |
|---|---|---|---|---|---|---|---|
| 1 | 6.493599 | 37 | −16.69946109 | −41.772 | −5.6635 | −17.632 | −4.46734967 |
| 1 | 6.645121 | 55 | −13.16411774 | −27.998 | −3.1656 | −11.813 | −4.104588151 |
| 1 | 6.404107 | 28 | −18.09615307 | −48.658 | −7.1336 | −1.0247 | −4.634540636 |
| 1 | 6.65908 | 46 | −15.16937238 | −34.885 | −4.3347 | −14.723 | −4.359451342 |
| 2 | 5.758972 | 37 | −18.91803374 | −40.617 | −5.8439 | −8.4381 | −5.697503272 |
| 2 | 5.879055 | 55 | −13.1730106 | −26.782 | −3.41 | −5.6545 | −4.08237026 |
| 3 | 5.921924 | 37 | −19.32477581 | −43.128 | −5.8176 | −18.589 | −6.493503982 |
| 3 | 6.316482 | 55 | −14.89303642 | −29.207 | −3.4284 | −12.622 | −5.347620864 |
| 4 | 4.926437 | 37 | −19.19118253 | −47.612 | −6.8235 | −4.9707 | −4.428226929 |
| 4 | 6.251435 | 55 | −16.26375592 | −33.626 | −3.8974 | −3.669 | −3.424338266 |
| 5 | 4.700764 | 37 | −16.75932916 | −46.735 | −7.1581 | −1.4198 | −3.330225727 |
| 5 | 6.235281 | 55 | −15.17467572 | −32.86 | −3.9622 | −18.829 | −2.882208655 |
| 6 | 4.758499 | 37 | −17.64374545 | −46.424 | −7.0057 | −3.9557 | −4.151263153 |
| 6 | 6.112713 | 55 | −15.67362999 | −32.584 | −4.0829 | −22.223 | −3.374865045 |
| 7 | 5.412774 | 37 | −18.84403557 | −55.293 | −7.027 | −6.2711 | −3.668593584 |
| 7 | 6.288939 | 55 | −18.14106706 | −41.451 | −4.0291 | −17.703 | −3.363972993 |
| 8 | 5.524343 | 37 | −19.44492457 | −54.993 | −6.8304 | −3.5904 | −3.568772209 |
| 8 | 6.401901 | 55 | −18.45326235 | −41.151 | −3.8827 | −15.812 | −3.349735215 |
| 9 | 5.698041 | 37 | −20.4938987 | −53.938 | −5.9418 | −6.7118 | −4.277208547 |
| 9 | 6.483438 | 55 | −19.17868955 | −40.035 | −3.2413 | −15.799 | −3.789398319 |
| 10 | 6.152152 | 37 | −19.27520474 | −49.099 | −9.9333 | −14.793 | −6.002278899 |
| 10 | 6.104575 | 55 | −15.63221011 | −35.019 | −6.6098 | −9.732 | −5.705765446 |
| 11 | 5.716302 | 37 | −21.77455825 | −51.143 | −9.916 | −8.1835 | −6.403441244 |
| 11 | 6.046932 | 55 | −17.25577763 | −37.107 | −6.5616 | −5.8321 | −5.378867074 |
| 12 | 6.541378 | 37 | −24.52809539 | −51.107 | −9.3771 | −17.176 | −10.80521603 |
| 12 | 6.751653 | 55 | −18.25979401 | −36.969 | −6.3782 | −12.102 | −8.057295998 |
| 12 | 6.334811 | 28 | −27.52736985 | −58.175 | −10.983 | −19.713 | −11.94168999 |
| 12 | 6.745367 | 46 | −21.43026192 | −44.038 | −7.8387 | −14.639 | −9.503891602 |
| 13 | 6.354415 | 37 | −23.18120623 | −46.299 | −5.0826 | −13.907 | −6.720039287 |
| 13 | 6.585083 | 55 | −17.26571175 | −32.504 | −2.848 | −8.8351 | −5.061446508 |
| 14 | 5.492402 | 37 | −21.55748754 | −46.768 | −5.6554 | −6.7765 | −5.325758114 |
| 14 | 6.172355 | 55 | −16.68349847 | −32.971 | −3.0592 | −4.4305 | −4.062337838 |
| 15 | 6.364534 | 37 | −25.41418931 | −47.566 | −5.2578 | −15.549 | −8.610489803 |
| 15 | 6.52458 | 55 | −18.75625553 | −33.693 | −2.9089 | −10.444 | −5.877435942 |
| 16 | 6.086519 | 37 | −22.8819649 | −49.768 | −5.0281 | −8.4316 | −4.865360384 |
| 16 | 6.717518 | 55 | −19.97321831 | −35.971 | −2.6673 | −14.746 | −3.84722431 |
| 17 | 5.517892 | 37 | −19.00207327 | −49.441 | −5.1463 | −4.469 | −4.153507101 |
| 17 | 6.661886 | 55 | −17.86082733 | −35.665 | −2.6814 | −17.211 | −3.40622034 |
| 18 | 5.947284 | 37 | −18.09801207 | −49.852 | −5.2373 | −7.5541 | −4.212835345 |
| 18 | 6.71578 | 55 | −18.00377806 | −35.99 | −2.7112 | −20.859 | −3.561363471 |
| 19 | 6.806991 | 37 | −28.29172329 | −39.408 | −1.3134 | −41.376 | −6.405634406 |

-continued

| Sequence | k_Hyb | T | dG_average | binding Dg | pfprobe | max(5'/ 3' free) | Dg_average_2 |
| --- | --- | --- | --- | --- | --- | --- | --- |
| 19 | 6.96155 | 55 | −22.16433101 | −25.736 | −0.87917 | −27.806 | −6.2915949 |
| 20 | 7.083721 | 37 | −34.8733754 | −44.416 | −0.76711 | −46.383 | −8.688773585 |
| 20 | 7.13876 | 55 | −27.25067955 | −30.401 | −0.47992 | −32.471 | −8.737169947 |
| 21 | 6.939231 | 37 | −33.23915941 | −37.506 | −0.82059 | −39.474 | −10.23622608 |
| 21 | 6.927577 | 55 | 23.28217285− | −23.757 | −0.441 | −25.828 | −9.127799158 |
| 22 | 7.112589 | 37 | −37.5616697 | −39.015 | −0.99673 | −40.983 | −15.67717349 |
| 22 | 7.102685 | 55 | −25.93534419 | −25.389 | −0.6085 | −27.459 | −12.45488968 |
| 23 | 6.372783 | 37 | −26.45689597 | −42.835 | −1.3538 | −10.915 | −5.450793737 |
| 23 | 6.944557 | 55 | −23.69447266 | −28.96 | −0.58986 | −31.031 | −5.816061771 |
| 24 | 6.215896 | 37 | −25.9709614 | −42.839 | −1.9715 | −10.4 | −5.207686436 |
| 24 | 6.995671 | 55 | −23.32301401 | −29.22 | −1.0313 | −31.29 | −5.701615276 |
| 25 | 6.714481 | 37 | −31.23487577 | −42.32 | −1.0855 | −23.685 | −7.099491319 |
| 25 | 7.027868 | 55 | −24.91471368 | −28.56 | −0.5824 | −30.631 | −7.013092143 |
| 26 | 6.38593 | 37 | −27.3905512 | −39.237 | −2.3169 | −41.205 | −5.415354031 |
| 26 | 6.806777 | 55 | −22.92353276 | −25.438 | −1.2373 | −27.509 | −6.540902946 |
| 27 | 6.579883 | 37 | −27.15977403 | −39.911 | −2.602 | −25.41 | −5.727915586 |
| 27 | 6.734515 | 55 | −20.95157137 | −26.029 | −1.664 | −17.14 | −5.317950766 |
| 28 | 6.860599 | 37 | −26.80159943 | −39.716 | −2.4901 | −19.254 | −5.494430375 |
| 28 | 7.174687 | 55 | −21.44914453 | −25.934 | −1.2424 | −28.004 | −5.043411424 |
| 29 | 6.195249 | 37 | −25.87191145 | −42.035 | −2.2299 | −15.891 | −5.238222299 |
| 29 | 6.942867 | 55 | −21.21304647 | −28.109 | −1.2381 | −30.179 | −4.993485145 |
| 30 | 6.811387 | 37 | −24.87789255 | −34.001 | −1.5688 | −15.295 | −5.44329072 |
| 31 | 6.643434 | 37 | −29.63771149 | −49.819 | −3.2141 | −9.9337 | −6.985684744 |
| 31 | 7.065788 | 55 | −22.54070203 | −36.112 | −1.7156 | −7.2312 | −5.092906075 |
| 32 | 6.084429 | 37 | −20.69936309 | −41.032 | −3.4047 | −11.228 | −5.086586389 |
| 32 | 6.925882 | 55 | −18.82320277 | −27.367 | −1.7422 | −29.437 | −3.82343689 |
| 33 | 5.780442 | 37 | −17.74581148 | −50.538 | −4.9237 | −15.607 | −3.390510457 |
| 33 | 6.71647 | 55 | −20.36527301 | −36.687 | −2.4407 | −11.237 | −3.886928135 |
| 34 | 6.864782 | 37 | −29.16611682 | −40.222 | −1.0342 | −19.027 | −7.355423553 |
| 34 | 7.194446 | 55 | −23.52963699 | −26.59 | −0.49414 | −28.661 | −7.145071361 |
| 35 | 6.30882 | 37 | −18.1699364 | −39.033 | −3.2304 | −7.5632 | −3.958629007 |
| 35 | 6.804477 | 55 | −18.26038676 | −25.315 | −1.4168 | −27.386 | −3.976988447 |
| 36 | 6.508046 | 37 | −22.07167661 | −34.411 | −1.8244 | −16.456 | −3.900994314 |
| 37 | 6.481893 | 37 | −27.13964671 | −39.955 | −2.2413 | −41.923 | −5.475190865 |
| 37 | 6.853413 | 55 | −22.21475651 | −26.117 | −1.1892 | −28.187 | −5.661913282 |
| 37 | 6.132725 | 28 | −27.74783493 | −46.874 | −3.0903 | −25.825 | −5.268975608 |
| 37 | 6.827725 | 46 | −25.35248021 | −33.036 | −1.6252 | −35.055 | −5.657714226 |
| 38 | 7.098691 | 37 | −29.1618495 | −41.063 | −0.00205 | −20.781 | −7.647254967 |
| 38 | 7.298904 | 55 | −22.67756282 | −27.451 | −0.54774 | −29.522 | −6.489019546 |
| 39 | 6.448974 | 37 | −27.27795942 | −43.91 | −2.8254 | −19.564 | −5.67255902 |
| 39 | 7.075777 | 55 | −22.30750708 | −30.132 | −1.4803 | −13.694 | −5.287102365 |
| 39 | 6.361354 | 28 | −28.38429871 | −50.798 | −3.8022 | −12.531 | −5.729724035 |
| 39 | 6.872587 | 46 | −25.28380899 | −37.021 | −2.0639 | −16.629 | −5.598896555 |
| 40 | 6.572649 | 37 | −26.01382104 | −38.641 | −2.2487 | −40.608 | −5.23926118 |
| 40 | 7.038522 | 55 | −21.14643517 | −24.865 | −1.2275 | −26.936 | −5.509088764 |
| 41 | 6.619415 | 37 | −24.89904202 | −42.185 | −3.478 | −14.907 | −4.976884579 |
| 41 | 7.119339 | 55 | −21.17484379 | −28.453 | −1.8266 | −10.328 | −4.622083254 |
| 42 | 6.234078 | 37 | −21.13565236 | −35.672 | −2.9729 | −17.6 | −4.678284585 |
| 43 | 6.164563 | 37 | −22.92308117 | −42.042 | −2.6259 | −0.96097 | −4.962054782 |
| 43 | 6.828428 | 55 | −20.30724322 | −28.11 | −1.2416 | −30.181 | −4.656494392 |
| 44 | 6.540634 | 37 | −29.69458582 | −39.594 | −1.9572 | −21.112 | −6.654721325 |
| 44 | 6.951088 | 55 | −23.54882189 | −25.932 | −1.0028 | −28.003 | −6.901939765 |
| 45 | 6.182305 | 37 | −24.13632028 | −44.397 | −1.9102 | −16.568 | −4.291761074 |
| 45 | 7.127481 | 55 | −23.26219179 | −30.526 | −0.94558 | −32.596 | −5.026341836 |
| 46 | 6.506334 | 37 | −24.49240493 | −42.716 | −1.6745 | −44.684 | −5.469966637 |
| 46 | 6.891185 | 55 | −24.52321065 | −28.934 | −0.62352 | −31.004 | −6.979206408 |
| 47 | 6.684362 | 37 | −14.03276311 | −54.997 | −5.9115 | 0 | −4.32595933 |
| 47 | 5.331332 | 55 | −13.85548219 | −40.789 | −3.2339 | −2.8701 | −3.744739899 |
| 48 | 6.081154 | 37 | −25.29976863 | −50.081 | −3.4615 | −20.024 | −4.5581571 0 |
| 48 | 6.866657 | 55 | −23.77897548 | −36.041 | −1.8933 | −38.112 | −4.628040149 |
| 49 | 6.420859 | 37 | −21.3806966 | −43.058 | −2.9457 | 0 | −4.22532639 |
| 49 | 6.969484 | 55 | −20.99919607 | −29.243 | −1.5576 | −31.314 | −4.382877842 |
| 50 | 6.377586 | 37 | −20.16876181 | −36.704 | −2.2026 | −22.446 | −4.191932856 |
| 50 | 6.836831 | 55 | −15.61179067 | −23.164 | −1.2289 | −25.234 | −3.41337009 |
| 51 | 6.388603 | 37 | −19.69215094 | −49.095 | −8.8813 | −21.973 | −5.410169781 |
| 51 | 6.704311 | 55 | −15.55700297 | −35.381 | −5.9143 | −15.732 | −4.912134016 |
| 52 | 5.701102 | 37 | −18.19188013 | −48.134 | −9.0318 | −10.19 | −8.442818444 |
| 52 | 6.303601 | 55 | −15.2514429 | −34.363 | −6.0454 | −7.392 | −4.870095249 |
| 53 | 6.516417 | 37 | −20.63824092 | −50.157 | −9.5625 | −22.66 | −6.144991218 |
| 53 | 6.750861 | 55 | −16.36516155 | −36.446 | −6.3348 | 16.378 | 5.280465471 |
| 54 | 5.734849 | 37 | −23.78206744 | −54.408 | −9.081 | −17.104 | −8.188236698 |
| 54 | 6.175647 | 55 | −20.47240221 | −40.451 | −5.683 | −12.659 | −8.270196835 |
| 55 | 4.437089 | 37 | −25.32774414 | −52.501 | −9.2594 | −7.8926 | −7.872486261 |
| 55 | 5.450797 | 55 | −18.86066495 | −38.549 | −5.9313 | −5.8203 | −5.912725069 |
| 56 | 6.523657 | 37 | −24.31994347 | −49.866 | −8.8287 | −13.075 | −10.51289077 |
| 56 | 6.542725 | 55 | −17.45275741 | −35.993 | −5.7153 | −8.7556 | −7.483788261 |

-continued

| Sequence | k_Hyb | T | dG_average | binding Dg | pfprobe | max(5'/ 3' free) | Dg_average_2 |
|---|---|---|---|---|---|---|---|
| 57 | 5.737655 | 37 | −25.26096992 | −51.468 | −8.151 | −25.084 | −7.729212877 |
| 57 | 6.56944 | 55 | −19.71512553 | −37.671 | −5.0515 | −18.107 | −6.842819887 |
| 58 | 5.869908 | 37 | −26.93831784 | −53.023 | −7.9007 | −12.987 | −7.391718053 |
| 58 | 6.428207 | 55 | −20.84849405 | −39.287 | −4.9493 | −9.4637 | −5.860494227 |
| 59 | 5.124995 | 37 | −23.18458 | −55.222 | −8.3928 | −29.379 | −5.869685748 |
| 59 | 6.336184 | 55 | −21.04092601 | −41.254 | −5.0525 | −22.251 | −6.138808531 |
| 60 | 5.783375 | 37 | −20.7797813 6 | −47.491 | −7.1478 | −18.35 | −5.821081755 |
| 60 | 6.637639 | 55 | −16.41606066 | −33.806 | −4.1634 | −13.634 | −4.072282545 |
| 61 | 5.658536 | 37 | −22.38310507 | −47.181 | −7.5475 | −8.3257 | −6.408472659 |
| 61 | 6.158557 | 55 | −17.28229897 | −33.529 | −4.3383 | −6.383 | −4.454339153 |
| 62 | 6.693126 | 37 | −24.31924855 | −47.491 | −7.6917 | −18.725 | −9.077606969 |
| 62 | 7.014858 | 55 | −18.91920666 | −33.806 | −4.4053 | −14.055 | −6.033626161 |
| 63 | 6.03039 | 37 | −31.84289221 | −46.697 | −3.0695 | −13.615 | −14.56183675 |
| 63 | 6.830978 | 55 | −23.99358341 | −32.774 | −1.5356 | −10.122 | −9.579511807 |
| 64 | 6.366036 | 37 | −26.07740681 | −45.039 | −4.0672 | −5.9236 | −6.618810546 |
| 64 | 6.853962 | 55 | −18.80396058 | −31.084 | −2.2064 | −4.3464 | −4.510062059 |
| 65 | 6.418173 | 37 | −25.28400363 | −43.946 | −3.5233 | −11.377 | −6.214304624 |
| 65 | 6.758708 | 55 | −19.22132148 | −29.985 | −1.9069 | −7.8872 | −4.711443428 |
| 65 | 6.323671 | 28 | −28.44631582 | −50.926 | −4.4953 | −13.121 | −6.870811953 |
| 65 | 6.693575 | 46 | −22.10342767 | −36.966 | −2.6499 | −9.6319 | −5.441748081 |
| 66 | 6.254255 | 37 | −24.43824541 | −47.975 | −4.5915 | −21.217 | −6.512154008 |
| 66 | 6.76502 | 55 | −19.64445666 | −34.173 | −2.3839 | −15.228 | −4.874223962 |
| 67 | 5.82361 | 37 | −24.18865054 | −47.03 | −4.9168 | −9.499 | −6.215419941 |
| 67 | 6.626818 | 55 | −18.2151185 | −33.289 | −2.6315 | −6.8234 | −4.455359547 |
| 68 | 5.601396 | 37 | −19.44394209 | −45.377 | −5.1255 | −19.132 | −4.146021699 |
| 68 | 6.581059 | 55 | −16.22596297 | −31.703 | −2.8537 | −13.313 | −3.642266878 |
| 70 | 6.159312 | 37 | −24.71995753 | −47.581 | −5.4923 | −12.296 | −6.253905672 |
| 70 | 6.947577 | 55 | −20.81145857 | −33.878 | −2.9372 | −13.69 | −5.018051995 |
| 70 | 5.897735 | 28 | −27.35539161 | −54.433 | −6.9047 | −14.217 | −7.008665359 |
| 70 | 6.499526 | 46 | −22.50863877 | −40.729 | −4.1486 | −10.375 | −5.573090768 |
| 71 | 6.123368 | 37 | −24.77989108 | −49.061 | −5.9752 | −5.9909 | −5.121741445 |
| 71 | 6.886395 | 55 | −20.88130794 | −35.321 | −3.1935 | −19.512 | −4.280191329 |
| 72 | 6.506021 | 37 | −25.77205652 | −48.954 | −5.211 | −12.751 | −6.362779345 |
| 72 | 6.938456 | 55 | −21.31104008 | −35.168 | −2.7314 | −24.315 | −4.812842442 |
| 73 | 6.928302 | 37 | −38.82914005 | −45.894 | −1.8656 | −47.862 | −10.10717616 |
| 73 | 7.310583 | 55 | −30.84704866 | −32.232 | −1.0033 | −34.303 | −11.63776512 |
| 74 | 6.422231 | 37 | −33.48181004 | −43.11 | −1.9843 | −45.077 | −7.865090386 |
| 74 | 7.027814 | 55 | −26.12883894 | −29.332 | −1.1539 | −31.403 | −8.081875887 |
| 75 | 6.979617 | 37 | −29.06302649 | −39.129 | −0.92277 | −41.097 | −6.499169819 |
| 75 | 7.137104 | 55 | −21.78479239 | −25.492 | −0.59567 | −27.562 | −5.821464987 |
| 76 | 6.291089 | 37 | −22.71969812 | −43.087 | −2.8092 | −12.037 | −4.12979974 |
| 76 | 6.686476 | 55 | −21.8839244 | −29.198 | −1.2608 | −31.268 | −4.825534358 |
| 76 | 5.963582 | 28 | −22.49897977 | −50.031 | −4.0407 | −12.276 | −4.047519533 |
| 76 | 6.509928 | 46 | −22.91340966 | −36.142 | −1.8937 | −13.99 | −4.428300729 |
| 77 | 5.874221 | 37 | −25.53986414 | −49.151 | −4.2985 | −10.324 | −5.026372156 |
| 77 | 6.699569 | 55 | −22.81659211 | −35.057 | −2.5185 | −17.008 | −5.149002384 |
| 78 | 5.081317 | 37 | −23.24868627 | −51.004 | −5.0915 | 0 | −4.983275299 |
| 78 | 6.243148 | 55 | −23.80418165 | −37.127 | −2.6035 | −21.302 | −4.893177948 |
| 79 | 4.220745 | 37 | −20.09979462 | −50.027 | −6.2036 | 0 | −4.974575965 |
| 79 | 6.221251 | 55 | −21.46606362 | −36.21 | −2.8928 | −9.4247 | −4.843784904 |
| 80 | 5.699717 | 37 | −30.63521783 | −49.782 | −4.6835 | −22.291 | −6.393951817 |
| 80 | 6.28254 | 55 | −26.03811048 | −36.026 | −2.4188 | −15.959 | −6.217263781 |
| 81 | 5.435628 | 37 | −17.47892435 | −52.004 | −5.4445 | −10.784 | −3.581000028 |
| 81 | 6.141796 | 55 | −15.89058724 | −38.127 | −2.9029 | −7.9388 | −3.127012976 |
| 82 | 4.490768 | 37 | −17.77322497 | −43.888 | −4.9679 | −4.6476 | −3.968110667 |
| 82 | 6.213266 | 55 | −16.37079568 | −30.179 | −2.3663 | −3.3254 | −3.286039565 |
| 82 | 5.156059 | 46 | −16.67898195 | −37.034 | −3.5201 | −3.9007 | −3.577181097 |
| 83 | 5.920113 | 37 | −22.39496242 | −52.113 | −3.0251 | −7.921 | −4.012456619 |
| 83 | 6.685215 | 55 | −22.64017573 | −37.971 | −1.5963 | −7.2936 | −4.177382083 |
| 84 | 6.409595 | 37 | −23.79565597 | −49.765 | −2.3335 | −7.1776 | −4.841827211 |
| 84 | 7.118607 | 55 | −21.77068055 | −35.996 | −1.0055 | −38.067 | −4.184045577 |
| 85 | 6.67084 | 37 | −21.50033636 | −45.113 | −4.4006 | −27.409 | −3.935994363 |
| 85 | 6.722208 | 55 | −18.00071051 | −31.359 | −2.3388 | −18.75 | −4.095268836 |
| 86 | 7.394846 | 37 | −24.9156486 | −50.702 | −2.3031 | −15.302 | −6.392169095 |
| 86 | 7.209255 | 55 | −22.01861156 | −36.982 | −1.1562 | −11.065 | −4.99275664 |
| 87 | 6.611552 | 37 | −31.5877987 | −52.126 | −3.5505 | −19.458 | −7.121974874 |
| 87 | 7.110619 | 55 | −27.3995776 | −38.414 | −1.7197 | −14.424 | −6.54765261 |
| 88 | 4.884468 | 37 | −16.30169957 | −49.385 | −5.8439 | −5.4214 | −5.446779655 |
| 88 | 5.869976 | 55 | −13.8171601 | −35.368 | −2.708 | −4.2097 | −4.248217977 |
| 89 | 6.582693 | 37 | −26.33891740 | −36.968 | −2.233 | −26.131 | −7.878803782 |
| 89 | 6.810758 | 55 | −19.15464541 | −23.223 | −1.2064 | −25.293 | −5.828278454 |
| 90 | 6.039519 | 37 | −27.31367875 | −44.708 | −2.8753 | −10.954 | −5.944350006 |
| 90 | 6.836369 | 55 | −24.92455266 | −31.036 | −1.3855 | −33.106 | −6.528264466 |
| 91 | 5.509794 | 37 | −19.68058646 | −54.437 | −6.7833 | −6.1258 | −3.778210659 |
| 91 | 6.201765 | 55 | −17.50082363 | −40.69 | −3.7937 | −4.8331 | −3.43536854 |
| 92 | 6.272034 | 37 | −28.70146551 | −50.279 | −3.9966 | −15.559 | −6.205580195 |

| Sequence | k_Hyb | T | dG_average | binding Dg | pfprobe | max(5'/3' free) | Dg_average_2 |
|---|---|---|---|---|---|---|---|
| 92 | 7.101642 | 55 | −26.72103301 | −36.448 | −1.8625 | −38.518 | −6.466232255 |
| 93 | 6.565171 | 37 | −30.97831029 | −47.513 | −3.0403 | −18.787 | −7.151679424 |
| 93 | 6.82859 | 55 | −25.30969944 | −33.707 | −1.593 | −12.977 | −6.600306619 |
| 94 | 5.815779 | 37 | −15.73269044 | −51.151 | −6.0932 | −8.5498 | −3.098197985 |
| 94 | 6.314285 | 55 | −14.54829421 | −37.393 | −3.5147 | −6.121 | −2.68477169 |
| 95 | 6.693808 | 37 | −36.26341953 | −48.948 | −2.0714 | −6.8182 | −9.199995825 |
| 95 | 7.412106 | 55 | −32.24715674 | −35.4 | −0.95865 | −37.47 | −11.08256153 |
| 96 | 6.874767 | 37 | −24.51210503 | −50.59 | −5.6869 | −4.5958 | −4.752012687 |
| 96 | 7.134715 | 55 | −18.06210693 | −36.724 | −3.1578 | −19.621 | −3.876489151 |
| 97 | 6.501341 | 37 | −33.40407013 | −50.666 | −3.521 | −14.442 | −7.037981446 |
| 97 | 6.9055 | 55 | −28.28637204 | −37.078 | −1.9548 | −13.545 | −6.761792623 |
| 98 | 6.817971 | 37 | −38.45842011 | −50.564 | −3.4668 | −34.027 | −10.07664379 |
| 98 | 7.302731 | 55 | −32.25886797 | −36.848 | −1.4805 | −38.918 | −9.86858742 |
| 99 | 6.026689 | 37 | −30.3137576 | −49.763 | −4.5807 | −6.0867 | −7.786580229 |
| 99 | 6.690746 | 55 | −23.16568785 | −35.815 | −2.3491 | −4.4087 | −5.580669209 |
| 100 | 4.431251 | 37 | −16.7137184 | −50.525 | −7.9263 | −2.5359 | −5.259399149 |
| 100 | 5.130717 | 55 | −13.84844443 | −36.917 | −4.2136 | −1.7544 | −3.851673493 |

Figure 9:
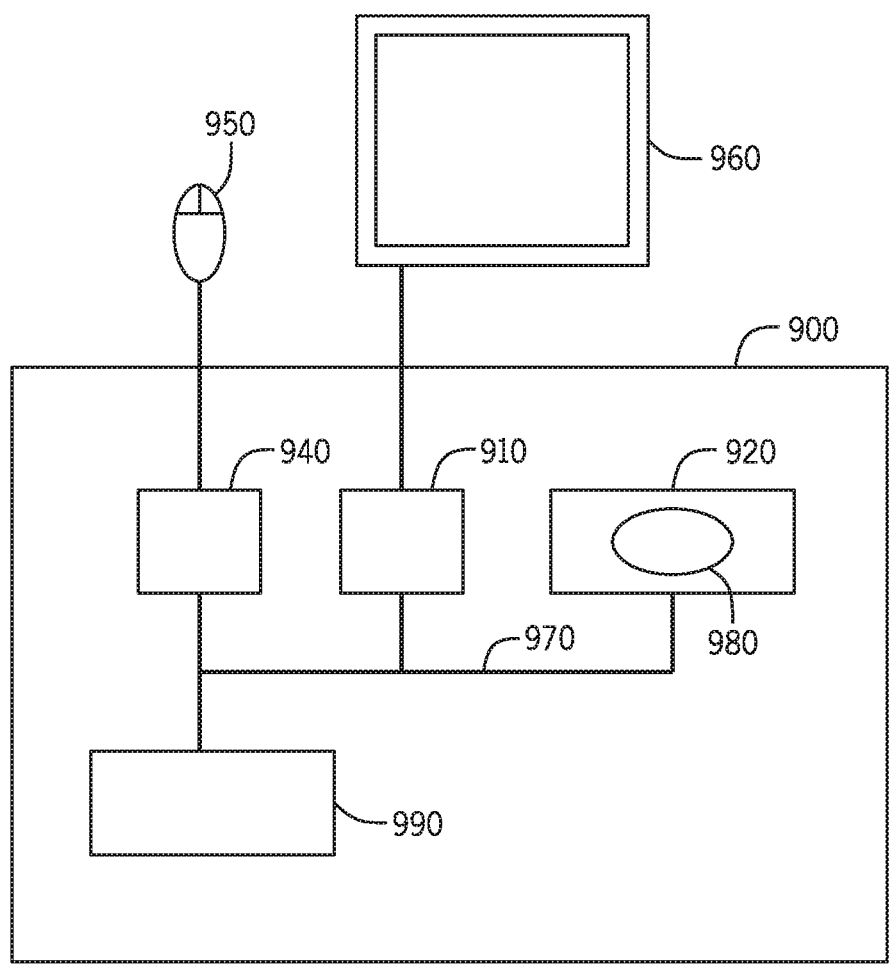
FIG. 9 illustrates an exemplary computing environment that can be used to carry out the method for predicting a hybridization rate constant of a first sequence according to an exemplary embodiment.

One or more of the techniques described herein for all figures can be implemented in or involve one or more computer systems. FIG. 9 illustrates a generalized example of a computing environment 900. The computing environment 900 is not intended to suggest any limitation as to scope of use or functionality of a described embodiment.

The computing environment 900 includes at least one processing unit 910 and memory 920. The processing unit 910 executes computer-executable instructions and can be a real or a virtual processor. In a multi-processing system, multiple processing units execute computer-executable instructions to increase processing power. The memory 920 can be volatile memory (e.g., registers, cache, RAM), non-volatile memory (e.g., ROM, EEPROM, flash memory, etc.), or some combination of the two. The memory 920 can store software 980 implementing described techniques.

A computing environment can have additional features. For example, the computing environment 900 includes storage 940, one or more input devices 950, one or more output devices 960, and one or more communication connections 990. An interconnection mechanism 970, such as a bus, controller, or network interconnects the components of the computing environment 900. Typically, operating system software or firmware (not shown) provides an operating environment for other software executing in the computing environment 900, and coordinates activities of the components of the computing environment 900.

The storage 940 can be removable or non-removable, and includes magnetic disks, magnetic tapes or cassettes, CD-ROMs, CD-RWs, DVDs, or any other medium which can be used to store information and which can be accessed within the computing environment 900. The storage 940 can store instructions for the software 980.

The input device(s) 950 can be a touch input device such as a keyboard, mouse, pen, trackball, touch screen, or game controller, a voice input device, a scanning device, a digital camera, remote control, or another device that provides input to the computing environment 900. The output device(s) 960 can be a display, television, monitor, printer, speaker, or another device that provides output from the computing environment 900.

The communication connection(s) 990 enable communication over a communication medium to another computing entity. The communication medium conveys information such as computer-executable instructions, audio or video information, or other data in a modulated data signal. A modulated data signal is a signal that has one or more of its characteristics set or changed in such a manner as to encode information in the signal. By way of example, and not limitation, communication media include wired or wireless techniques implemented with an electrical, optical, RF, infrared, acoustic, or other carrier.

Implementations can be described in the general context of computer-readable media. Computer-readable media are any available media that can be accessed within a computing environment. By way of example, and not limitation, within the computing environment 900, computer-readable media include memory 920, storage 940, communication media, and combinations of any of the above.

Of course, FIG. 9 illustrates computing environment 900, display device 960, and input device 950 as separate devices for ease of identification only. Computing environment 900, display device 960, and input device 950 can be separate devices (e.g., a personal computer connected by wires to a monitor and mouse), can be integrated in a single device (e.g., a mobile device with a touch-display, such as a smartphone or a tablet), or any combination of devices (e.g., a computing device operatively coupled to a touch-screen display device, a plurality of computing devices attached to a single display device and input device, etc.). Computing environment 900 can be a set-top box, personal computer, or one or more servers, for example a farm of networked servers, a clustered server environment, or a cloud network of computing devices.

Having described and illustrated the principles of our invention with reference to the described embodiments, it will be recognized that the described embodiments can be modified in arrangement and detail without departing from such principles. It should be understood that the programs, processes, or methods described herein are not related or limited to any particular type of computing environment, unless indicated otherwise. Various types of general purpose or specialized computing environments can be used with or perform operations in accordance with the teachings described herein. Elements of the described embodiments shown in software can be implemented in hardware and vice versa.

Discussion below is based on model construction based on using dGavg, Temperature, Pap, nGp, Gb, and Pm as the features 18.

Figure 10A:
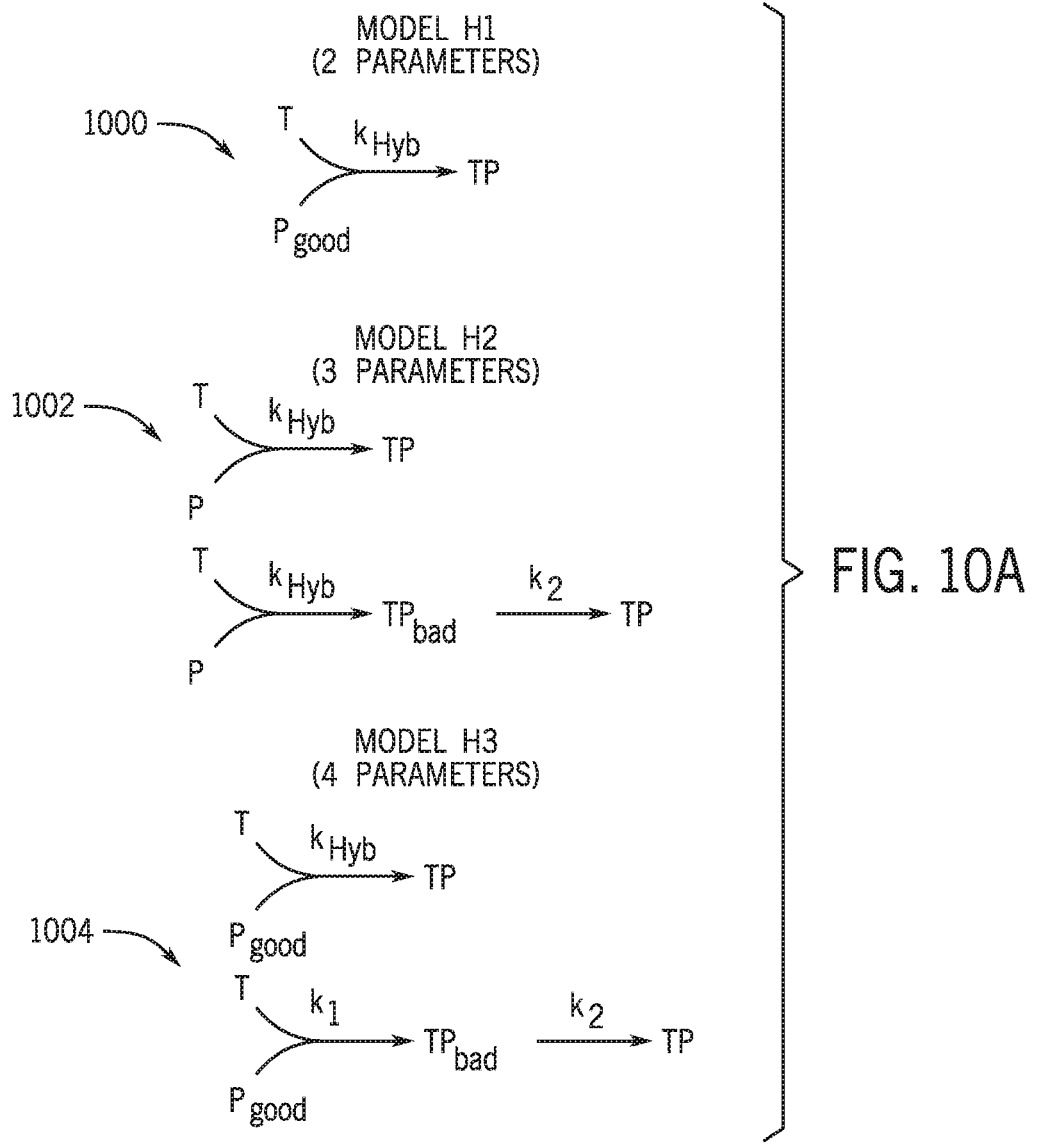
FIG. 10a illustrates three different reaction models considered for fitting rate constant kHyb to fluorescence kinetics data.

Turning now to FIG. 10a, the figure illustrates three different reaction models 1000, 1002, 1004, considered for fitting rate constant $k_{Hyb}$ to fluorescence kinetics data. Model H1(e.g., model 1000) is the simplest model and has 2 free parameters: $k_{Hyb}$ and $[P_{good}]$. $[P_{good}]$ denotes the concentration of properly synthesized probes that are capable of hybridization, with the remainder of the [P] assumed to be unhybridizable and constitutively fluorescent. Model H2 (e.g., model 1002) has 3 free parameters: $k_{Hyb}$, $k_1$, and $k_2$. Model H3 (e.g., model 1004) has 4 parameters: $k_{Hyb}$, $[P_{good}]$, $k_1$, and $k_2$. An even simpler model H0 with only $k_{Hyb}$ as a parameter appears to fail to reasonably fit the observed fluorescence data.

Figure 10B:
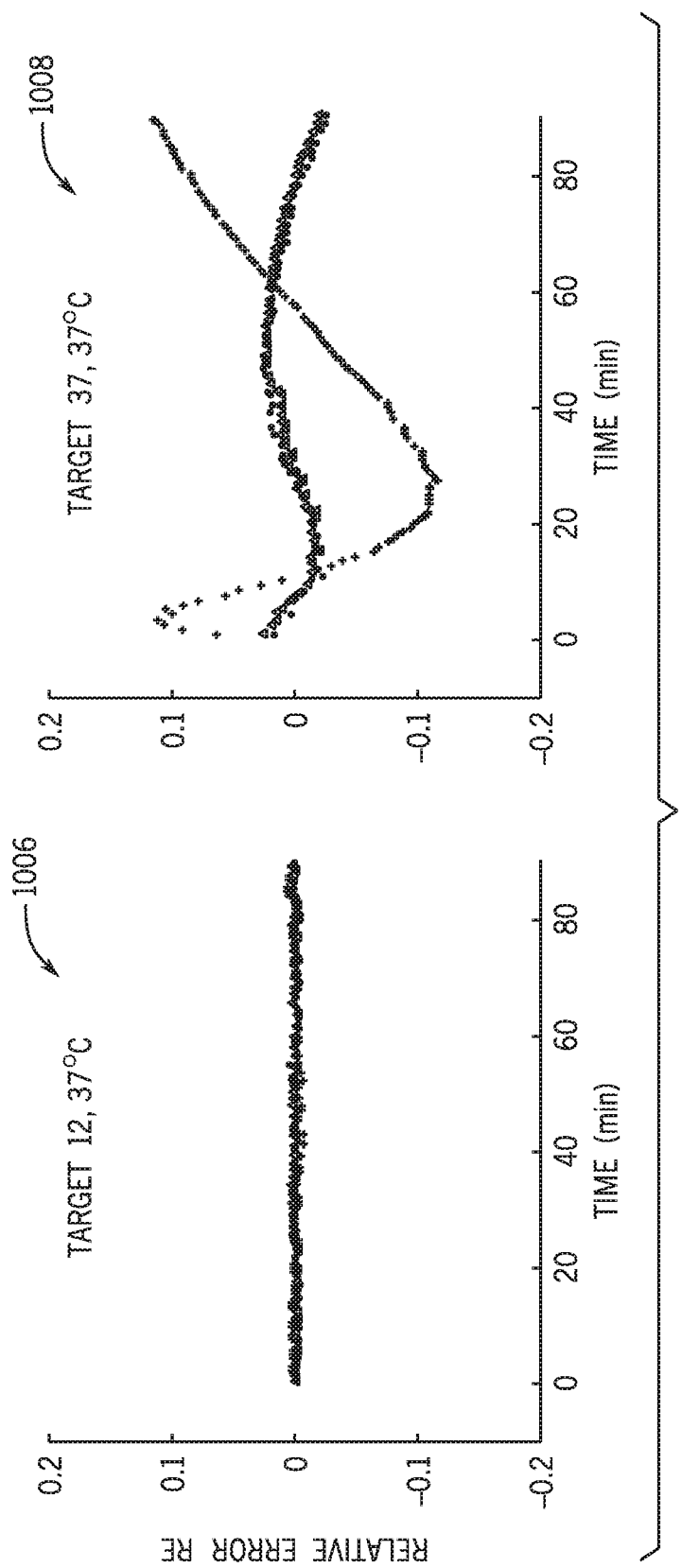

FIG. 10b illustrates two examples 1006, 1008 of fit quality for the 3 reaction models 1000, 1002, and 1004. The y-axis of FIG. 10b plots the relative error RE as a function of time for each model 1000, 1002, and 1004 using best-fit parameters. For Target 12 (e.g., target number 12 of all targets 16), all three models 1000, 1002, and 1004 show low relative error across all time points, but model 1000 is significantly worse than 1002 and 1004 for Target 37 (e.g., target 37 of all targets 16).

Figure 10C:
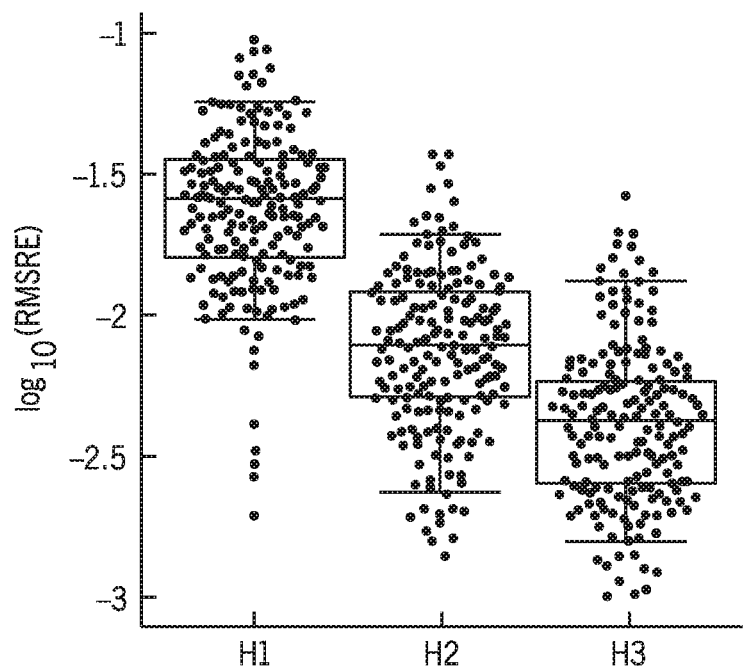
FIG. 10c illustrates a summary of fit performance of the three models of FIG. 10a across all 210 fluorescence kinetics experiments.
Figure 10D:
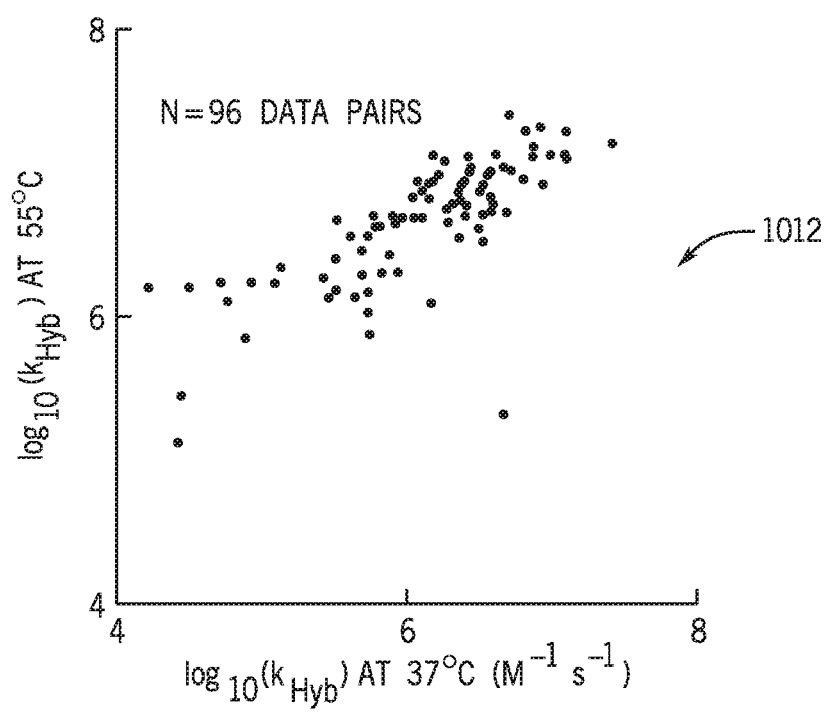
FIG. 10d illustrates examples of observed rate constants for 96 targets at 37° C. and 55° C.

FIG. 10c illustrates a summary of fit performance for the three models 1000, 1002, 1004, across all 210 fluorescence kinetics experiments. Each point in graph 1010 corresponds to the root mean square relative error (RMSRE) of all time points for a particular fluorescence experiment. Based on this result, we chose to proceed with H3 and its best-fit $k_{Hyb}$ values for all subsequent studies. FIG. 10d illustrates a graph 1012 of observed rate constants for 96 targets at 37° C. and 55° C. 4 of the targets did not stably bind to their corresponding probes at 55° C. due to being A/T rich and were not included in the graph 1012.

FIG. 11a illustrates rate constant prediction using a Weighted Neighbor Voting (WNV) model. More specifically, the figure illustrates values 1100 of a number of rationally designed features are computed based on the sequences of the target 16 and probe 210, as well as the reaction conditions (temperature, salinity). Shown in the figure is an example calculation for feature Gb, the weighted average $\Delta G°$ of the hybridized complex. The $\Delta G°$ of formation for a number of likely states $S_a$ are computed using Nupack, and subsequently used to compute their probability of existence at equilibrium $Pr(S_a)$.

Figure 11C:
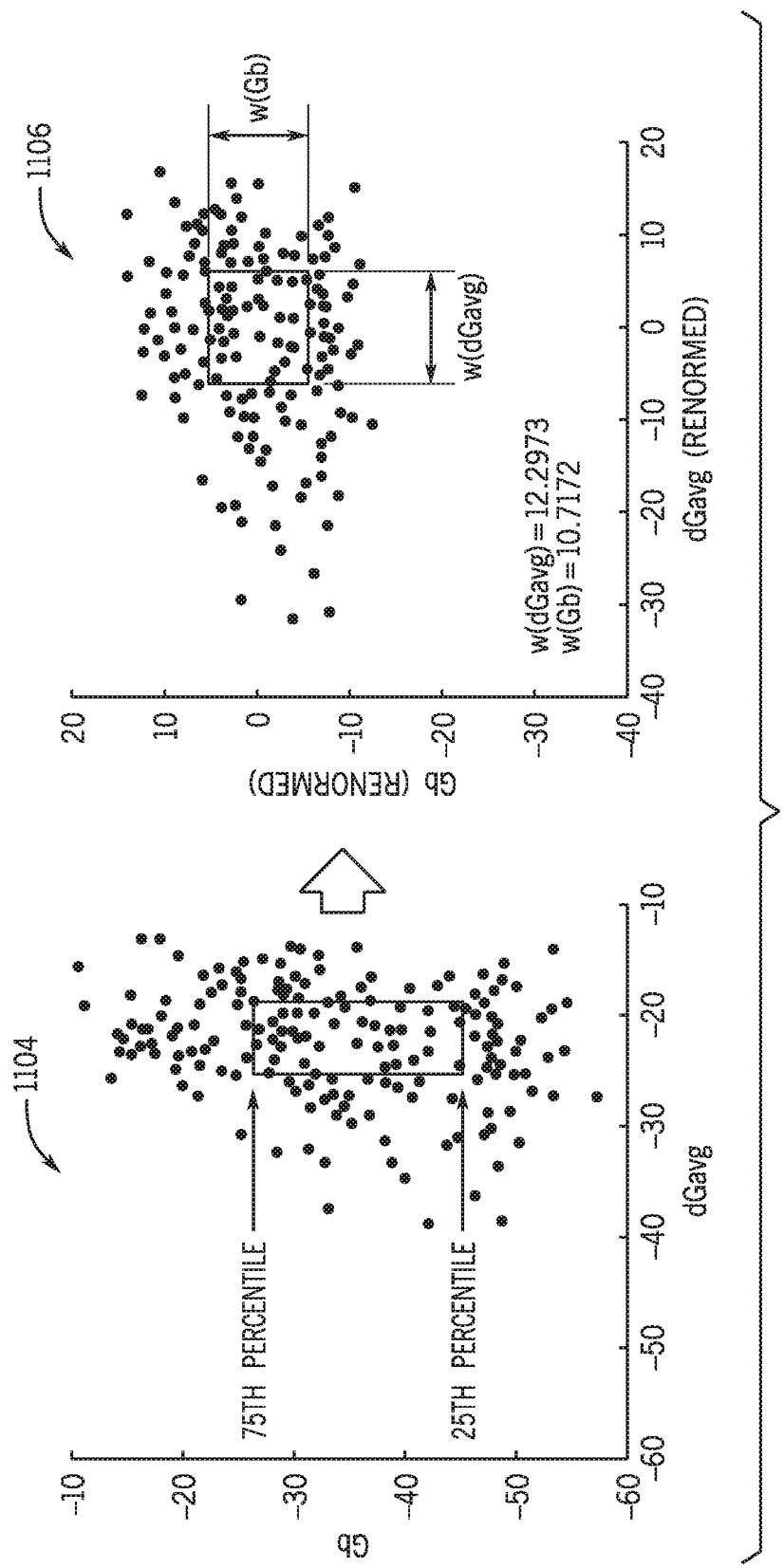
FIG. 11c illustrates example feature renormalization based on 75th and $25^{th}$ percentile values.

FIG. 11b illustrates a graph 1102 having an example relationship between the base-10 logarithm of the experimental hybridization rate constants kHyb (based on reaction model 1004) vs. Gb values for the 210 hybridization experiments. There is moderate correlation between $k_{Hyb}$ and Gb, indicating that Gb may be an effective feature for rate constant prediction. FIG. 11c illustrates feature renormalization based on 75th and $25^{th}$ percentile values. Plotted on graph 1104 are the raw values of the Gb (e.g., weighted average $\Delta G°$ of the hybridized complex, such as TP complex) and dGavg features 18 for all 210 experiments. These feature 18 values are linearly transformed (re-normalized), as shown on graph 1106, based on a set of feature weights w(i): The 75th percentile value of a feature i is renormalized to $$+\frac{w(i)}{2}$$

and the 25th percentile value is renormalized to $$-\frac{w(i)}{2}.$$

Figure 11D:
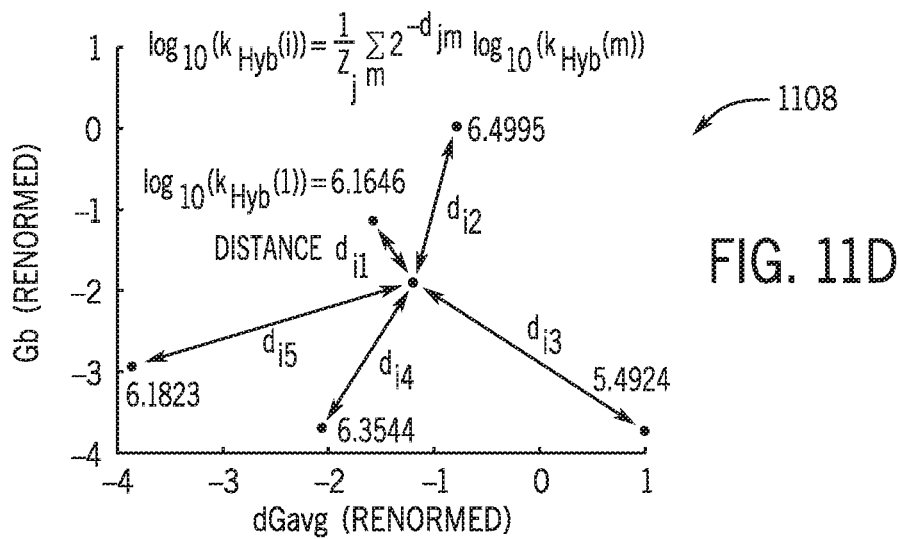
FIG. 11d illustrates an example graph showing distances for a reaction whose rate constant $k_{Hyb}$ is to be predicted.

FIG. 11d illustrates a graph 1108 showing that given a reaction whose rate constant $k_{Hyb}$ is to be predicted (middle dot), the reaction's renormalized feature values are first calculated and compared to the feature values of reactions with known $k_{Hyb}$ values (dots surrounding middle dot). The feature space distance $d_jm$ between the unknown reaction j and each known reaction m is used to determine the prediction weight of reaction m. Prediction weight drops exponentially with distance and is calculated as $2^{-d_{j,m}}$; $Z_j$ is the sum of all prediction weights involving j. Both the predicted rate constant $k_{Hyb}$ and the known rate constants are expressed in logarithm base10.

Figure 11E:
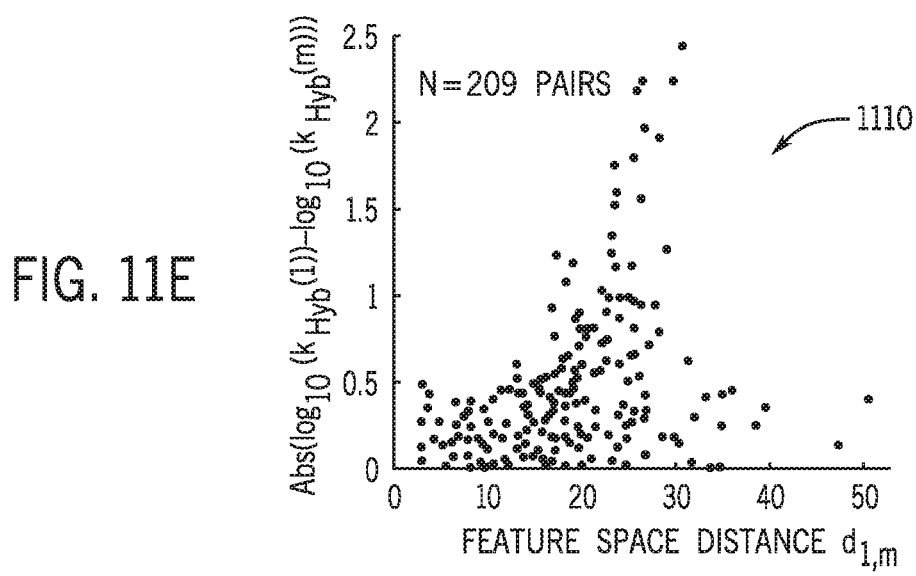
FIG. 11e illustrates an example graph showing relationship between feature space distance d and the absolute value of difference in experimental rate constants (log 10) for two hybridization reactions.

FIG. 11e illustrates a graph 1110 showing relationship between feature space distance d and the absolute value of difference in experimental rate constants (log 10) for two hybridization reactions. Here, feature space distances are calculated using the final 6-feature model (see FIG. 12), for one reaction (arbitrarily assigned j=1) vs. all 209 other reactions. Pairs of reactions with small d generally have similar rate constants. The converse statement is not true because two very different reactions may coincidentally have similar rate constants.

Figure 11F:
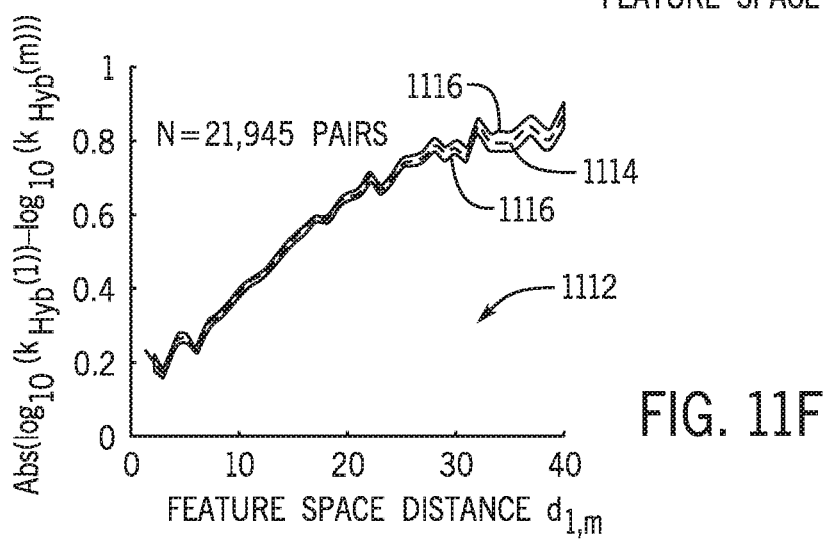
FIG. 11f illustrates a summary plot of Abs($\log_{10}(k_{Hyb}(j))-\log_{10}(k_{Hyb}(m))$) vs. feature distance $d_{j,m}$.

FIG. 11f illustrates a summary plot 1112 of $Abs(\log_{10}(k_{Hyb}(j))-\log_{10}(k_{Hyb}(m)))$ vs. feature distance $d_{j,m}$ for all $$\frac{210}{2}$$

pairs of experiments. A black line 1114 shows the mean and a region 1116 shows ±1 standard deviation on the mean.

Figure 12A:
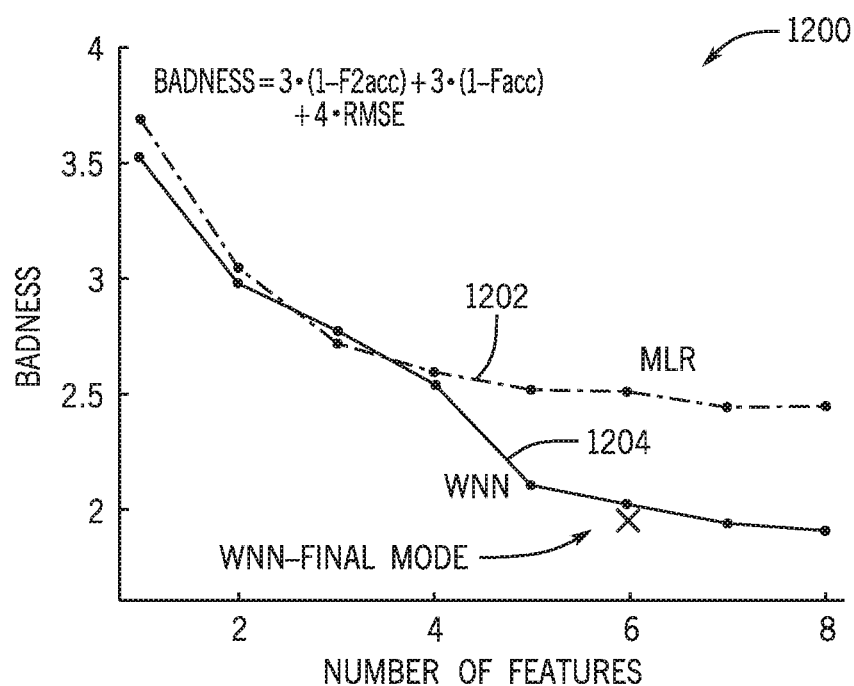
FIG. 12a illustrates example prediction accuracy of a WNV model.

FIG. 12a illustrates prediction accuracy of a WNV model. For example, a graph 1200 is shown, with curves 1202 and 1204. The dots of curve 1204 show the results of a greedy optimization algorithm in which individual weight-optimized features are sequentially added to the WNV model. The Badness metric (y-axis) is calculated based on the fraction accurate to within a factor of 2 (F2acc), fraction accurate to within a factor of 3 (F3acc), and the root-mean-square error (RMSE). The final 6-feature WNV model (labeled 'X') comprise the 6 features from the 8-feature model with the largest weights. Performance of a multilinear regression (MLR) model is also shown in curve 1202 for comparison.

Figure 12B:
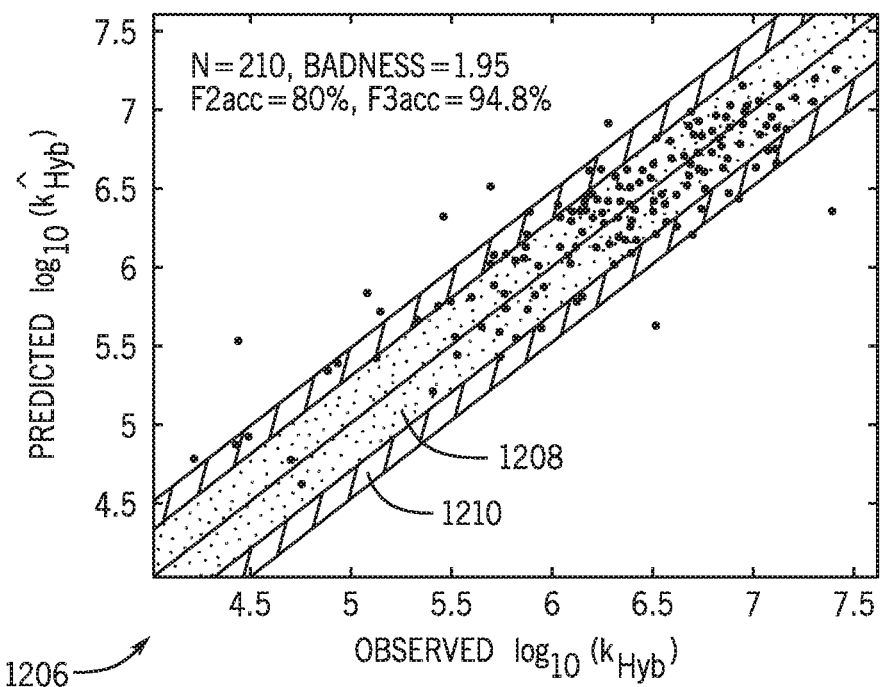
FIG. 12b illustrates rate constant prediction performance of a final WNV model.

FIG. 12b includes a graph 1206 illustrating rate constant prediction performance of the final WNV model, using feature weights that were optimized on all 210 experimental reactions. Each dot corresponds to the prediction of each reaction's rate constant based on the data from the other 209 reactions' rate constants. A shaded region 1208 indicates correctness to within a factor of 2, and a shaded region 1210 indicates correctness to within a factor of 3.

Figure 12C:
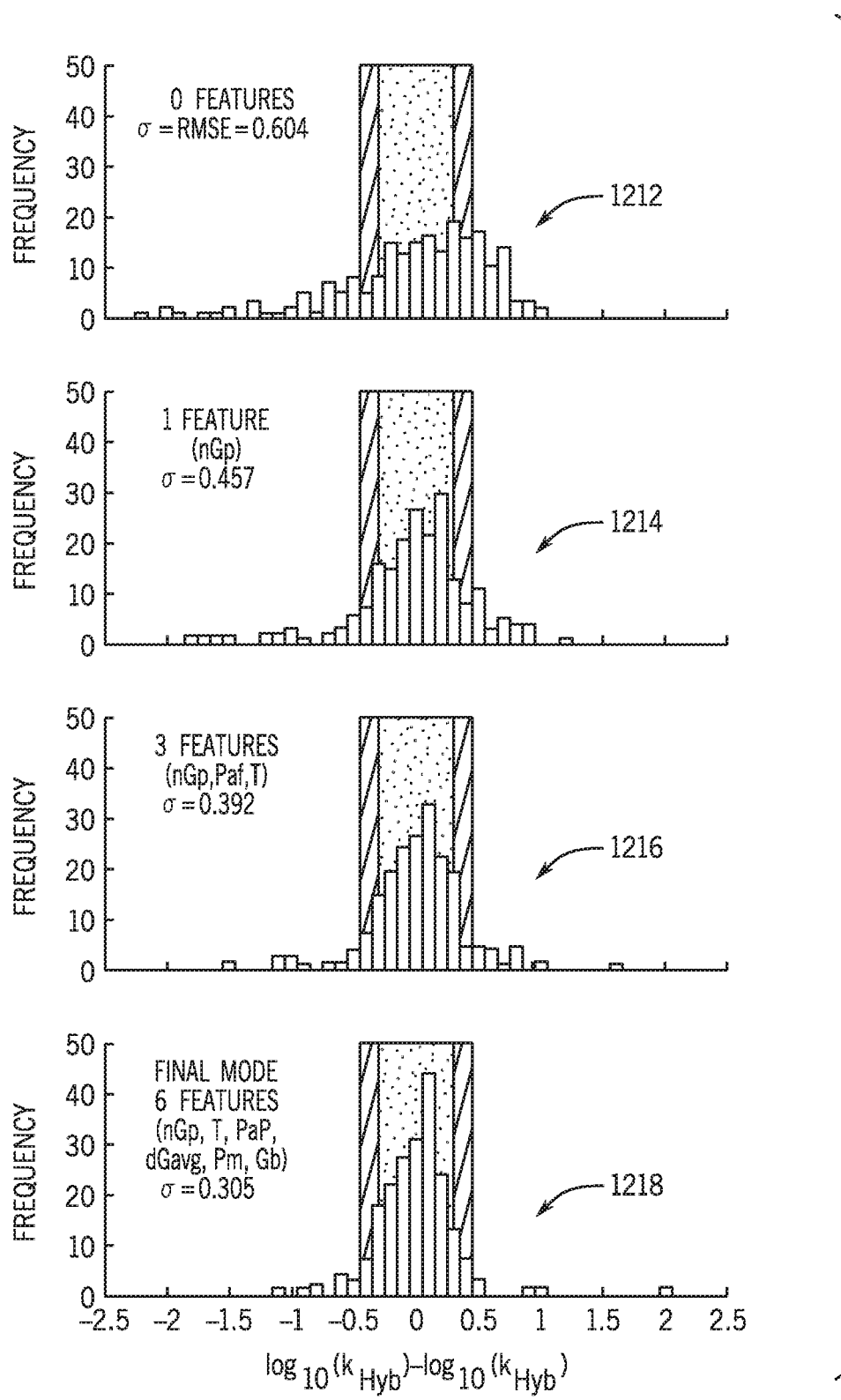
FIG. 12c illustrates histograms of an example WNV model using 0, 1, 3, and 6 features.

FIG. 12c illustrates embodiments of histograms 1212, 1214, 1216, and 1218 of experimental minus predicted $\log_{10}(k_{Hyb})$ values for WNV model using 0, 1, 3, and 6 features. The 0-feature model represents a naive model predicting the same $\log_{10}(k_{Hyb})$ value for all sequences, and the 1-feature model represents a simple model that considers only secondary structure.

Figure 12D:
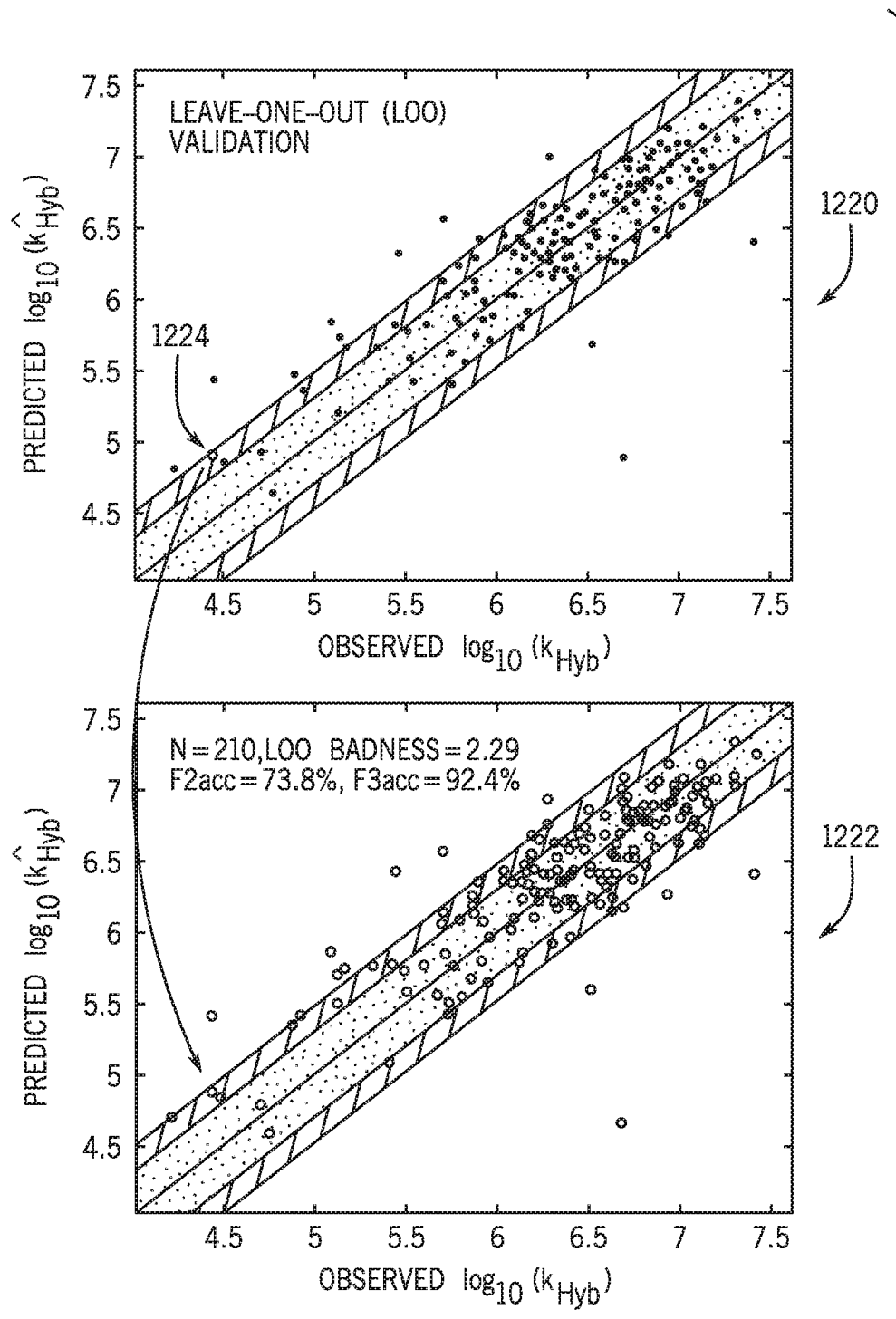
FIG. 12d illustrates example leave-one-out (LOO) validation via graphs.

FIG. 12d illustrates leave-one-out (LOO) validation via graphs 1220 and 1222. More specifically, to estimate the accuracy of the final WNV model on prediction of rate constants for new sequences, LOO validation was performed. In graph 1220, feature weights were optimized on the 209 data points, and this model was used to predict the rate constant of a single "unknown" data point 1224. The bottom panel summarizes the prediction performance of the 210 distinct models (with weights optimized on different sets of 209 points).

Figure 13A:
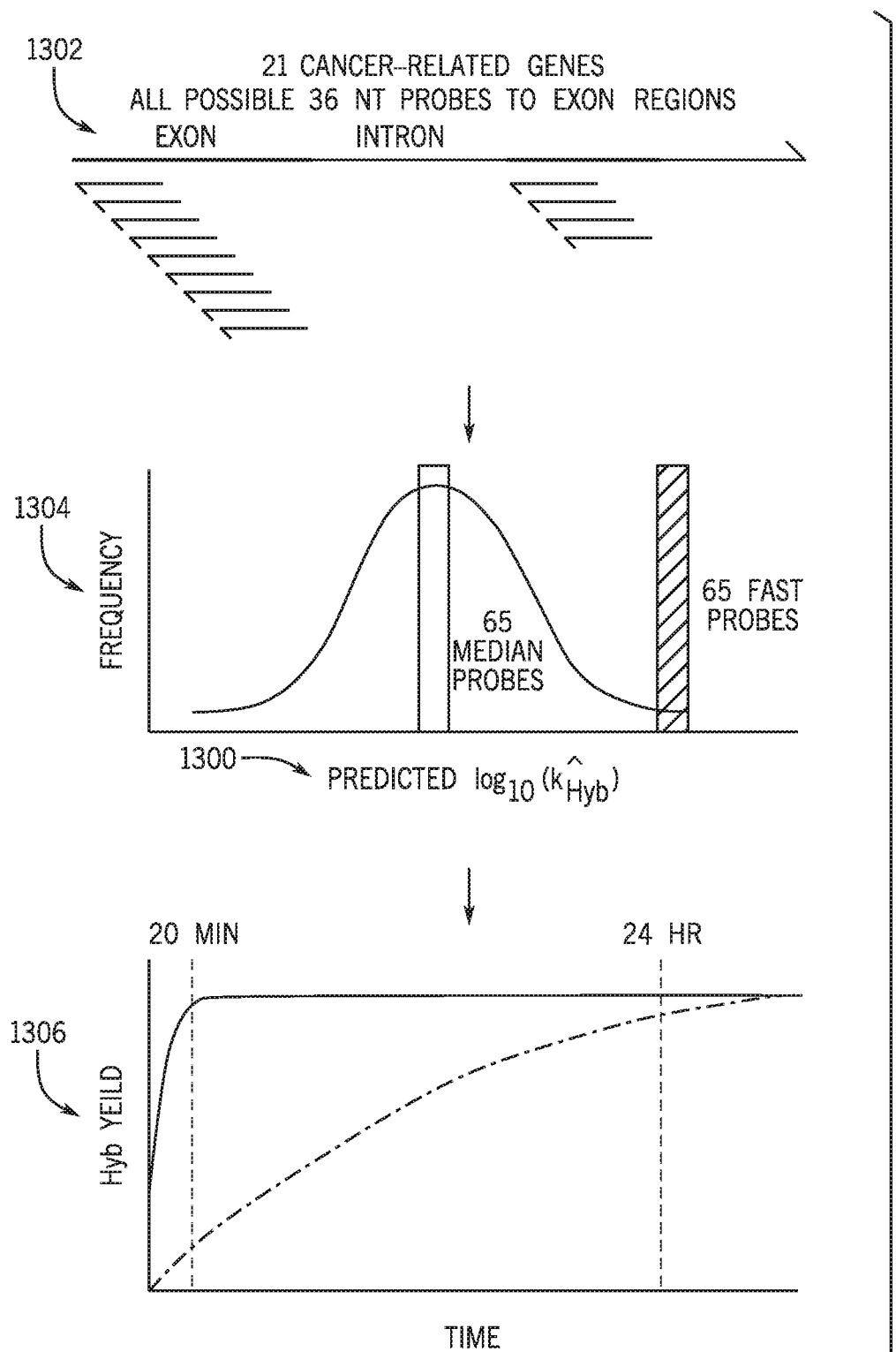
FIG. 13a illustrates example, hybridization rate constant $k_{Hyb}$ predicted for all possible 36-mer hybridization probes to exon regions of 21 cancer-related genes.

FIGS. 13a-d illustrates comparison of probes predicted to possess median vs. fast hybridization kinetics for enrichment from human genomic DNA. For example, FIG. 13a illustrates hybridization rate constant $k_{Hyb}$ 1300 predicted for all possible 36-mer hybridization probes to exon regions of 21 cancer-related genes 1302. Middle graph 1304 and lower graph 1306 express the idea behind probe selection and library design, but are for example only and may not accurately reflect kinetics distributions or trajectories of any particular gene or probe.

Figure 13B:
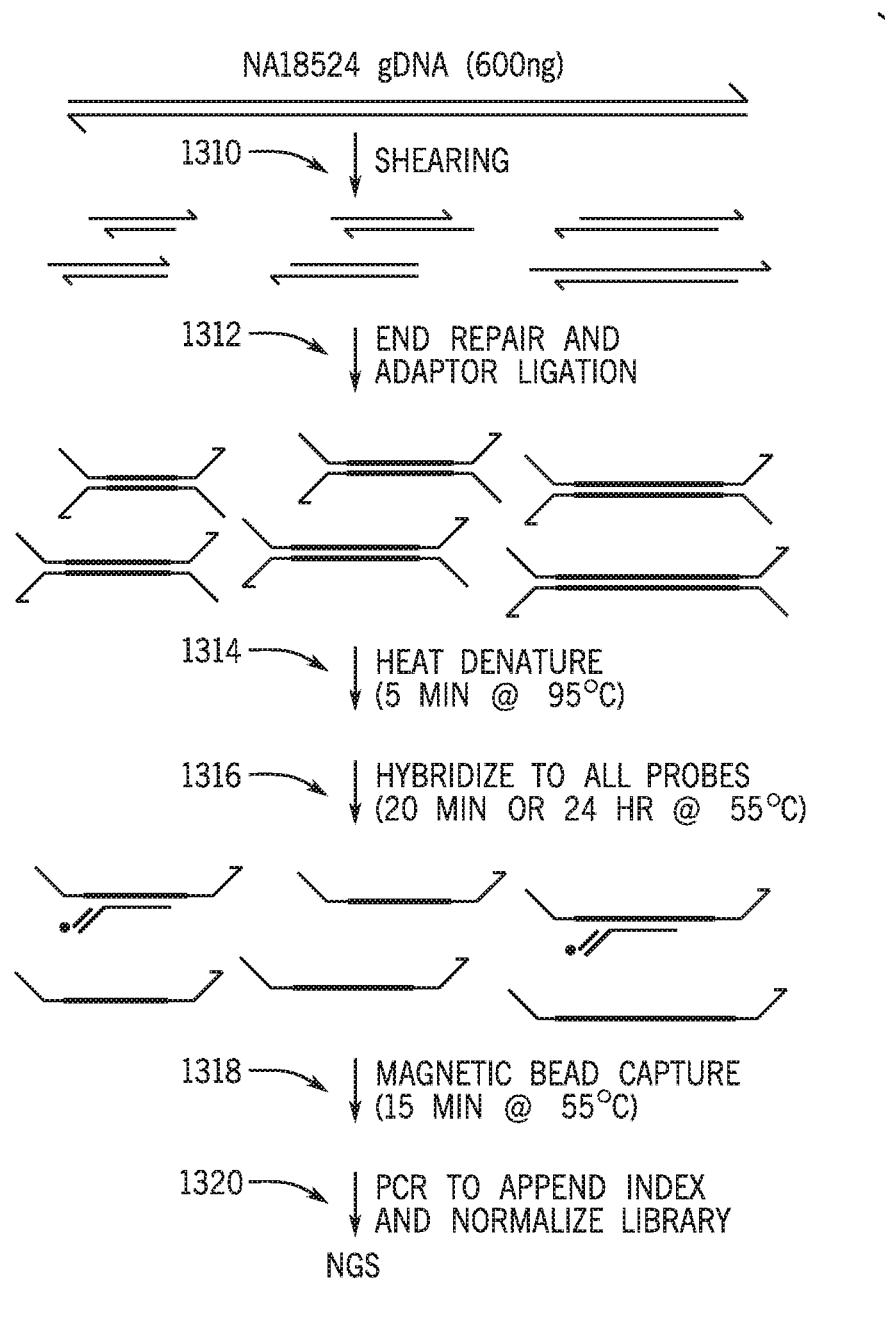
FIG. 13b illustrates embodiments of a genomic DNA enrichment and a library preparation workflow.

FIG. 13b illustrates a genomic DNA enrichment and library preparation workflow 1308. As shown, the workflow includes a shearing stage (block 1310), an end repair and adaptor ligation stage (block 1312), a heat denature stage (block 1314), a hybrizing of all probes stage (block 1316), a magnetic bead capture stage (block 1318), and a PCR to append index and normalize library stage (block 1320). All hybridization probes were present at 50 pM concentration.

Figure 13C:
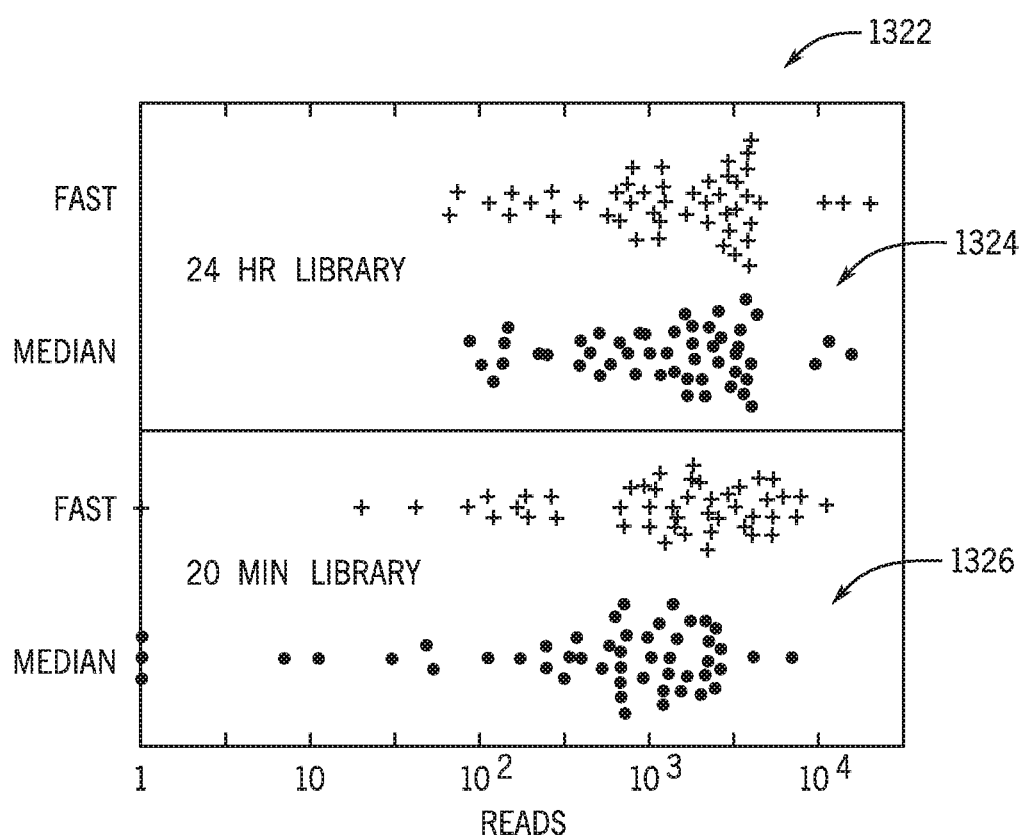
FIG. 13c illustrates a Beeswarm plot embodiment of NGS reads aligned to certain probes.

FIG. 13c illustrates a Beeswarm plot 1322 of NGS reads aligned to each probe, excluding 15 fast and 15 median probes to 4 genes with low read depth. In the library in which probes were hybridized to the fragmented gDNA for 24 hours (top panel 1324), there is no significant difference in the read count distribution between the median and fast probes. In the 20 minute hybridization library shown in bottom panel 1326, the fast probes showed significantly higher reads than the median probes, indicating that the probes the algorithm predicted to be faster did in fact provide a higher degree of hybridization within 20 minutes.

Figure 13D:
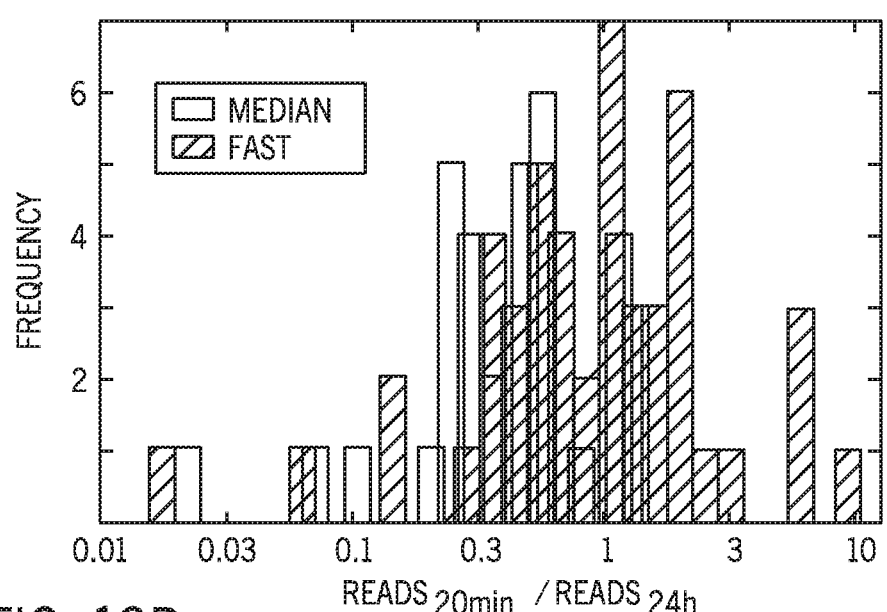
FIG. 13d illustrates an example ratio of aligned reads in a 20 minute library to a 24 hour library for certain probes.

FIG. 13d illustrates a ratio of aligned reads in the 20 minute library to the 24 hour library for each probe. A high ratio indicates fast hybridization kinetics; ratio can exceed 1 because libraries were normalized, so that fast probes are more dominant and occupy more reads in the 20 minute library.

Details of Model Construction—Hybridization rate constant (kHyb) fitting.

Turning back to FIG. 10a, from the experimental kinetics traces (e.g., traces 220 shown in FIG. 2d), we wish to determine a single rate constant kHyb that describes the dominant hybridization kinetics pathway. However, a simple two-state T+P→TP reaction model fails to reasonably capture a significant portion of the kinetic behavior. Most notably, over 40% of the observed reactions appeared to asymptote to a final reaction yield of less than 85%, based on positive and negative control fluorescence values. Consequently, we considered 3 slightly more complex reaction models 1000, 1002, 1004 of hybridization, in order to evaluate which best fits the observed data, as shown in FIG. 10a.

Model H1 1000 assumes that the T+P→TP reaction is correct, but that a fraction of the probes P are poorly synthesized, or otherwise incapable of proper hybridization with target T or the accompanying fluorescence quenching. Thus, in addition to kHyb, H1 has one extra fitting parameter: $[P_{good}]0$, the initial concentration (or fraction) of viable probe P.

Model H2 1002, in contrast, assumes that all probe P is correctly synthesized, but that some fraction of the T+P reaction undergoes an alternative pathway with rate constant k1 to result in a state $TP_{bad}$ with high fluorescence. This frustrated state $TP_{bad}$ may represent states in which T and P are co-localized by misaligned base pairs. Model H2 1002 assumes that $TP_{bad}$ undergoes first-order rearrangement with rate constant $k_2$ to form the correct product TP. Model H2 1002 has a total of 3 fitting parameters: $k_{Hyb}$, $k^1$, and $k_2$. Model H3 1004 is a simple combination of models H1 1000 and H2 1002, wherein there exists both a fraction of poorly synthesized P as well as the alternative pathway involving $TP_{bad}$, and has a total of 4 fitting parameters: $k_{Hyb}$, $[P_{good}]0$, $k_1$, and $k_2$.

For each of our 210 fluorescence kinetics experiments, we used a custom stochastic fitting function to determine the best-fit values of each rate constant parameter for each model. Here, best-fit is determined as the minimal sum-of-square relative error RE, where $$RE = \left(\frac{\text{Data} - \text{Simulation}}{\text{Data}}\right).$$

Minimum and maximum fluorescence values corresponding to 0% and 100% yields were determined through separate control experiments. FIG. 10b shows RE values of best-fit parameters for two hybridization reactions. While all three models describe the observed fluorescence data well for some reactions, other reactions show a significant difference among the three models.

For each hybridization reaction, we have between 60 and 180 RE values, each corresponding to a time point at which fluorescence was measured. The RE values of each hybridization experiment are summarized as a single root mean square relative error (RMSRE) value, defined as $$RMSRE = \sqrt{\frac{1}{\alpha}\Sigma_t RE(t)^2}$$

where a is the total number of time points t during which fluorescence was measured for the reaction. FIG. 10c shows the distribution of RMSRE values for each hybridization model; model H3 1004 appears to give the best overall fit to the data. More complex reaction models where also evaluated, with additional fitting parameters, but these did not significantly improve RMSRE over model H3 1004 (data not shown). Consequently, model H3's best-fit $k_{Hyb}$ rate constants were used for all subsequent work.

FIG. 10d summarizes Model H3's best-fit $k_{Hyb}$ values for paired hybridization experiments at 37° C. and 55° C. The values of $k_{Hyb}$ ranged roughly 3 orders of magnitude at both temperatures. Even among relatively fast reactions corresponding to target/probe sequences with relatively low secondary structure, there is still significant variation in hybridization kinetics. The large diversity of $k_{Hyb}$ values for different sequences and the imperfect correlation between rate constants for the same sequence at different temperatures emphasizes the difficulty and need for a predictive kinetics model, such as the models described herein.

Weighted Neighbor Voting (WNV) Model.

To predict the rate constant of a new hybridization reaction, a WNV model checks the reaction for similarity against labeled instances (hybridization reactions with known rate constants) in an existing database (e.g., database 20), and allow each instance in the database to make a weighted "vote." Instances that are more similar to the new reaction are weighted more heavily.

To quantitate the similarity or dissimilarity between two hybridization reactions, we abstract each reaction into a number of features. The value of each feature for a particular hybridization reaction is computable based on the sequences of the target and probe, and the reaction temperature and buffer conditions. Each hybridization reaction is thus a point in feature space. With an optimally designed and weighted set of features, the two points close in feature space should exhibit similar $k_{Hyb}$ values. The converse is not necessarily true: two hybridization reactions with coincidentally similar $k_{Hyb}$ values may possess very different feature values.

As mentioned previously, mapping the hybridization reactions into feature space is important because targets that are similar in sequence space may not have similar hybridization kinetics, and vice versa, due to the sensitivity of secondary structure to small changes in DNA sequence in certain regions, but not in others. For example, oligonucleotide (2) with sequence "ACACACACTTAAAAT-TGTGTGTGTCCC" (SEQ ID NO: 104) has higher Hamming distance to oligo (1) with sequence "ACACACACTTTTTTTTGTGTGTGTCCC" (SEQ ID NO: 105) than oligo (3) with sequence "ACTCA-GACTTTTTTTTGTGTGTGTCCC" (SEQ ID NO: 106), but is expected to exhibit much more similar kinetics in hybridization to each's respective complement. In this case, one possible feature could be the number of base pairs formed in the hairpin stem of the minimum free energy structure: oligos (1) and (2) would have feature value 8, while oligo (3) would have feature value 6.

There are many potential approaches to the prediction of an analog desired parameter ($k_{Hyb}$ in this application) based on a set of features, the simplest of which is multilinear regression (MLR). WNV was selected because WNV may significantly outperform MLR when the relationships between the desired parameter and the features are nonlinear. Simultaneously, WNV is a highly scalable framework, in the sense that additional labeled instances can easily be incorporated for improved prediction accuracy without requiring reoptimization of model parameters (feature weights).

Feature Construction and Normalization.

Starting by rationally designing 38 potential features, each based on some aspect of DNA biophysics that it is believed may influence kinetics. FIG. 11a shows Gb, one of the 6 features used in a final model; Gb can be thought of as the weighted average of the #G# of formation of the TP complex, based on probabilities of state existence/occupancy at equilibrium. FIG. 11b shows the relationship between the observed $k_{Hyb}$ (according to model H3 1004) and the value of Gb. There is significant correlation between $k_{Hyb}$ and Gb; simultaneously, the relationship is not clearly linear. There may not be good physical interpretations of all effective features—in these cases, the feature in question is likely correlated with a yet-undiscovered complex feature with a firm physical basis.

The features constructed had different units and different ranges of values. In order to calculate the distance between two hybridization reactions, it may be necessary to normalize the different features into a consistent scale. Because the distributions of most feature values were distinctively non-Gaussian for the 210 reactions, normalization was performed based on the interquartile range: the 75th percentile feature value is mapped to a score of $$+\frac{w(i)}{2},$$

and the $25^{th}$ percentile value is mapped to $$+\frac{w(i)}{2}$$

(FIG. 11c), where w(i) is the weight of feature i. The feature space distance $d_{j,m}$ between an unknown reaction j and a known reaction m is calculated as a Euclidean distance:

$$d_{i,j} = \sqrt{\Sigma_i (f_i(j) - f_i(m))^2}$$

where $f_i(j)$ is the value of renormalized feature i for reaction j (FIG. 4d). Because a feature i with larger weight w(i) allows a larger range of scores, it can contribute more to the distance between two hybridization reactions. FIGS. 11e and f confirm that the difference in $k_{Hyb}$ values for a pair of reactions increases with feature space distance d.

Rate Constant Prediction.

From a database of hybridization experiments m with known $k_{Hyb}(m)$ and renormalized feature values, the WNV model makes the following prediction for $k_{Hyb}(j)$ of an unknown hybridization reaction j:

$$\log_{10}(k_{Hyb}(j)) = \frac{1}{Z_j} \Sigma_m 2^{-d_{j,m}} \cdot \log_{10}(k_{Hyb}(m))$$

where $\Sigma_m 2^{-d_{j,m}}$ is the "partition function" of the distances involving reaction j.

To quantitate the overall performance of a particular WNV model (defined by its set of features and corresponding feature weights w(i)), the following "Badness" metric may be constructed:

Badness=3·(1−F2acc)+3−(1−F3acc)+4·RMSE where F2acc is the fraction all predicted reactions j in which predicted $k_{Hyb}(j)$ and the experimental $k_{Hyb}(j)$ agrees to within a factor of 2, F3acc the fraction that agrees to within a factor of 3, and $$RMSE = \sqrt{\frac{1}{N}\Sigma_j \left(\log_{10}(k_{Hyb}(j)) - \log_{10}(k_{Hyb}(j))\right)^2}$$

is the root mean square error of the logarithm of the hybridization rate constant (where N=210 is the number of experiments).

The Badness metric was chosen rather than RMSE only (i.e. a least-squares fit) because it may be more relevant for many applications involving the design of DNA oligonucleotide probes and primers: Rather than marginally improving the predictions of outlier sequences that are off by more than an order of magnitude, the Badness metric as described above emphasizes instead improving the fraction of predictions that are correct to within a factor of 3, or better yet within a factor of 2. Simultaneously, to allow efficient computational optimization of feature weights, the Badness metric to be minimized may not be locally flat, so RMSE is included as a component of Badness. Use of different Badness metrics may result in optimized feature weights that exhibit a different tradeoff between the magnitude and frequency of large prediction errors.

Feature Selection and Weighting.

All 38 potential features constructed showed significant correlation with kHyb, but it may be inappropriate to include all of these in the WNV prediction model both because several features may consider redundant information, and because large sets of feature weights are computationally difficult to optimize. It may be useful to first manually prune the list of potential features down to 17 most promising features, based on single-feature WNV performance (using each feature's optimized feature weight). Due to the complexity and nonlinearity of the Badness landscape over the feature weight parameter space, it may not be feasible to determine an analytic solution of optimal weights. Instead, it may be useful to use a stochastic numerical optimization algorithm to find weight values that achieve Badness minima.

Next, a greedy algorithm may be implemented in which individual features that best improve the Badness at each round are iteratively added to an initially empty feature set. FIG. 12a shows that the Badness decreases as the number of features included increases up to 8; at 9 features, the WNV model shows no additional Badness improvement. Also plotted in FIG. 12a are the Badness of for MLR model using various numbers of features. Up to 4 features, the WNV and MLR models provide similar prediction accuracies; however, WNV continues improving with additional features whereas MLR performance plateaus.

The optimized feature weights for the 8-feature WNV model includes two features very small weights (w<0.1); these may be removed, and the resulting WNV model consist of the following 6 features: dGavg, Pap, Gb, T, nGp, and Pm, with weights of 12.30, 11.89, 10.72, 6.88, 6.54, and 0.94, respectively. A brief text description of these each feature follows. dGavg corresponds to the sum of the ΔG° of binding for all subsequences of the target weighted by the probability of all nucleotides of the subsequence being unpaired. Pap corresponds to the sum of the probability-weighted ΔG° of the strongest continuous subsequence that is expected to be unpaired. Gb was described with respect to FIG. 11a and corresponds to the sum of the probability-weighted ΔG° of formation of the target-probe complex. T is the reaction temperature in Celsius. nGp corresponds to the partition function energy of the probe secondary structure, as calculated by Nupack. Pm is similar to Pap, but is calculated for misaligned target-probe complexes.

FIG. 12b shows the accuracy of the final 6-feature WNV model. Each blue dot plots the predicted $\log_{10}(k_{Hyb})$ value vs. the experimentally observed $\log_{10}(k_{Hyb})$ value for a single hybridization experiment. Each prediction was performed using 209 labeled instances (all reactions except the one to be predicted), using the feature weights trained on all 210 data points. Predictions were accurate to within a factor of 2 for 80% of the reactions, and within a factor of 3 for 94.8% of the reactions. For comparison, FIG. 12c shows histograms of the distribution of prediction errors in $\log_{10}(k_{Hyb})$ for WNV models using 0, 1, 3, and 6 features.

Leave-One-Out Validation of Final WNV Model.

The fact that the final model's feature weights were fitted to all 210 experiments raises potential concern regarding whether the WNV model's prediction accuracy would generalize to new hybridization reactions, because the latter's (unknown) rate constant may not be used for training feature weights. It may be beneficial to perform leave-one-out (LOO) validation on the model to study the generalizability of the WNV model.

Accordingly, in LOO studies, 210 separate feature weight optimizations were performed, each using a different set of 209 hybridization experiments. Thus, each of the 210 models possessed different feature weights, and each model was used to predict the hybridization rate constants of the single hybridization experiment not included for its feature weight optimization (dot 1224 in top panel 1220 of FIG. 12d). The aggregate performance of these 210 LOO models are shown in the bottom panel 1222 of FIG. 12d. F2acc and F3acc are marginally lower than in FIG. 5b at 73.8% and 92.4%, respectively.

Applicants in order to help the research community predict hybridization rate constants for DNA oligo probes and primers, have constructed a web-based software tool, available at http://nablab.rice.edu/nabtools/kinetics The software typically completes predicting kHyb within 30 seconds, with the bulk of the computing time devoted to computation of the Pap and Pm feature values. It is currently seeded with the 210 hybridization experiment results performed in this paper, but will be updated with additional hybridization experiment results in the future, which should further improve prediction accuracy.

Enrichment from Human Genomic DNA.

The human genome is over 3 billion nucleotides long, but the coding regions that form the exome collectively only span 30 million nucleotides, or 1% of the genome. Within the 20,000 genes of the exome, typically there are only between 10-400 are that are relevant to any particular disease. Consequently, solid-phase enrichment of relevant gene regions using highly multiplexed hybridization of synthetic DNA oligonucleotide probes may be a preferred approach for targeted sequencing.

Current commercial multiplex hybrid-capture panels generally use a very large number of synthetic probe oligonucleotides to fully tile or overlap-tile the genomic regions of interest; for example, the whole exome requires more than 200,000 distinct oligonucleotide probe species. Due to the large number of oligo species involved, the concentration of each species is thus necessarily quite low (tens of picomolar), resulting in hybrid-capture protocols that typically span at least 4 hours, and more frequently more than 16 hours. Because of the varying hybridization kinetics of different probes (FIG. 10d), it is likely that many probes do not contribute significantly to hybridization yield, and in fact slow down the hybrid-capture process by forcing lower concentrations of the fast-hybridizing probes.

To experimentally test this possibility, we first applied our hybridization rate constant prediction algorithm to all possible 36 nt probes to exon regions of 21 genes. Because the exon regions are typically 3000 nt long, this corresponds to roughly 3000 possible probes. Predicted rate constants typically range about 2 orders of magnitude, with the fast (≥95th percentile) probes being typically a factor of 3 faster than median probes (~$50^{th}$ percentile). NGS hybrid-capture enrichment typically uses probes longer than 36 nt (e.g. Agilent SureSelect uses 120 nt probes), but there is likely a similar if not greater range of hybridization kinetics rate constants for longer probes due to the greater possibility of secondary structure and nonspecific interactions.

Subsequently, a total of 65 fast probes and 65 median probes may be picked across the exon regions of 21 different cancer-related genes. The expectation is that after a 24 hour hybridization protocol, the fast and median probes would produce similar reads, but with a short 20 minute hybridization protocol, the fast probes would exhibit significantly greater reads than median probes (FIG. 13a). A library preparation protocol is summarized in FIG. 13b; all 130 probes are hybridized to the adaptor-ligated DNA simultaneously. However, the number of reads aligned to a particular probe is not directly proportional to its hybridization yield, due to well-documented sequencing bias. For example, some adaptor-ligated amplicons exhibit significant secondary structure and is less efficiently PCR amplified during normalization, or less efficiently sequenced due to lower flow cell binding efficiency. For this reason, 15 fast and 15 median probes targeting 4 genes resulted in less than 100× sequencing depth, and were excluded from subsequent analysis. It is not believed this to affect the conclusions from the genomic DNA enrichment study performed.

Comparison of reads for the 20 minute hybridization library and for the 24 hour hybridization library indicates that the probes predicted to be fast on average exhibited both a 2-fold increase in reads in the 20 minute library, and a 2-fold increase in the ratio of reads at 20 min vs. 24 hours. This is slightly worse than the algorithm's predicted 3-fold difference between median and fast probes, but understandable given that the rate constant prediction algorithm was trained on single-plex hybridization rather than on multiplex hybridization. Subsequent calibration experiments indicate that the correlation constant between single-plex and multiplex $k_{Hyb}$ values are roughly $r^2=0.6$.

Results thus suggest that sparse hybrid-capture enrichment panels would produce faster kinetics at a significantly lower cost. Rather than fully tiling or overlap-tiling the genetic regions of interest, it would be better to use a higher concentration of a few probes with fastest hybridization kinetics. Multiple probes appear to only be needed insofar as biological genomic DNA may be fragmented, and a different probe is needed to capture each fragment. With the notable exception of cell-free DNA, most genomic DNA from clinical samples are longer than 500 nucleotides.

The concentrations of the probes used for this application was 50 pM per probe, and was intentionally selected so as to be similar to the concentrations of probes used by commercial enrichment kit providers At 50 pM concentrations, up to 200,000 probes can be used and the total oligo concentration would still be at a reasonable 10 µM. At the significantly (e.g. 10×) higher individual probe concentrations that become feasible with a sparse coverage of target genetic regions, even the 20 minutes allotted here for hybridization could be further reduced, greatly speeding up the NGS library preparation workflow from current practice of 4-24 hours.

Summary Discussion and Technical Effects

In the instant application, we combined the rational design of features and the WNV framework with computational optimization of feature selection and feature weights, resulting in a final model that is capable of accurately predicting hybridization kinetics rate constants based on sequence and temperature information. The final WNV rate constant prediction model is highly scalable and easily incorporates new experimental data to provide improved predictions, without requiring model retraining. With every additional hybridization experiment and its accompanying fitted kHyb value, the 6-dimensional feature space becomes denser, ensuring that on average a new hybridization experiment will be closer to an existing labeled instance. Thus, prediction accuracy will further increase and as additional hybridization kinetics data is further collected.

To seed the model with a reliable initial database of labeled instances that is representative of the diversity of genomic DNA sequences, applicants experimentally characterized the kinetics of 210 hybridization experiments across 100 biological target sequences using fluorescence. The X-probe architecture allowed more economically study kinetics for a reasonably large number of target sequences, but extra nucleotides of the universal arms may cause hybridization kinetics to differ slightly from that of a standard single-stranded probe. For example, there may be a systematic bias towards lower rate constants because of the reduced diffusion constants. Nonetheless, because all targets/probes use the same universal arm sequences, it is likely that the relative ordering of rate constants is preserved.

Research was started with 38 rationally designed features that were eventually pruned down to 6 in the final model. The high LOO validation accuracy of the WNV model indicates that these features capture a significant, if not majority, portion of the complexity of the hybridization process. Simultaneously, there remain pairs of experiments in our database with similar feature values (feature space distance d≤3) but with 3-fold differences in $k_{Hyb}$.

The hybridization reactions experimentally characterized in the work were all performed in 5×PBS buffer, and all target and probe sequences were 36 nt long. These experiment constraints were designed to reduce the diversity of hybridization reactions, in order to ease the training of the WNV model. Additionally, with genomic DNA targets, the long-range secondary structure and the fragmentation pattern of genomic DNA targets should also be considered. An expanded model to accommodate varying length targets and probes (including targets overhangs) and other buffer conditions will require the construction of new features.

Multiplex hybrid-capture panels for enriching target regions from genomic DNA is commonly used in targeted sequencing for scientific and clinical studies. In the absence of reliable kinetics prediction software, researchers and companies have taken a brute-force probe design approach, using fully tiled or overlapping-tiled probes to cover genetic loci of interest. While this approach ensures the presence of at least some fast-binding probes, it is both expensive (in terms of synthesis and QC of thousands of probes) and results in slower workflows. Accurately predicting multiplexed hybridization kinetics will enable precision design of sparse, high-performance probe panels for target enrichment.

It may be beneficial to list some equations as they may improve understanding of the claimed subject as follows:

$F=a \cdot \Delta G°_{pf}+b$ may apply to bioinformatic features that comprise one or more features based on a first calculated ensemble standard free energy of the first nucleic acid molecule, a second calculated ensemble standard free energy of the second nucleic acid molecule, or a third calculated ensemble standard free energy of a duplex formed through hybridization of the first and second nucleic acid molecules at the reaction temperature and the reaction buffer conditions.

$F=a \cdot \Delta G°_{mfe}+b$ may apply to bioinformatic features that comprise one or more features based on a first calculated standard free energy of a minimum free energy structure (mfe) of the first nucleic acid molecule, a second calculated standard free energy of the mfe of the second nucleic acid molecule, or a third calculated standard free energy of the mfe of a duplex formed through hybridization of the first and second nucleic acid molecules at the reaction temperature and the reaction buffer conditions.

$F=a \cdot (\Delta G°_{pf}-\Delta G°_{mfe})+b$ may apply to bioinformatic features that comprise one or more features based on a difference between a calculated ensemble standard free energy and a calculated standard free energy of the mfe of a duplex formed through hybridization of the first and second nucleic acid molecules at the reaction temperature and the reaction buffer conditions.

$F=a \cdot \min\{\Delta G°(i:i+N-1)\}+b$ may apply to bioinformatic features comprise one or more features based on a calculated standard free energy of strongest-binding N nucleotide subsequence of the first nucleic acid molecule at the reaction temperature and the reaction buffer conditions.

$F = a \cdot \max\{P_{open}(i:i+N-1)\} + b$ may apply to bioinformatic features that comprise one or more features based on a calculated maximum probability of a N nucleotide subsequence of the first nucleic acid molecule being all in unpaired states at equilibrium.

$F = a \cdot \max\{P_{open}(i:i+N-1) \cdot \Delta G°(i:i+N-1)\} + b$ may apply to bioinformatic features that comprise one or more features based on a calculated maximum probability-weighted standard free energy of binding of a N nucleotide subsequence of the first nucleic acid molecule being all in unpaired states at equilibrium.

In view of the many possible embodiments to which the principles of our invention can be applied, we claim as our invention all such embodiments as can come within the scope and spirit of the following claims and equivalents thereto.

The invention claimed is:

1. A method for predicting a rate constant of a desired hybridization reaction given sequences of a first nucleic acid molecule and a second nucleic acid molecule, a reaction temperature, and a reaction buffer, the method comprising:
   storing a database consisting of ten or less columns for storing bioinformatics features of the desired hybridization reaction, each column storing a different bioinformatics feature, wherein rows of the database are written based on data acquired by performing hybridization experiments on a plurality of hybridization reactions having known rate constants, the data acquired consisting of values for the rows storing the bioinformatics features;
   calculating a plurality of feature values for a number of bioinformatic features of the desired hybridization reaction;
   calculating distances between the plurality of feature values and corresponding database rate constant values stored in the database;
   calculating a weighted average of a logarithm of the corresponding database rate constant values, with larger weights assigned to value instances having values closer in distance to the plurality of feature values of the desired hybridization reaction;
   providing the weighted average as a predicted logarithm of the rate constant of the desired hybridization reaction; and
   selecting at least one candidate probe sequence to use with a target sequence from a plurality of probe sequences based on the predicted logarithm of the rate constant.

2. The method of claim 1, wherein the bioinformatic features comprise one or more features based on a first calculated ensemble standard free energy of the first nucleic acid molecule, a second calculated ensemble standard free energy of the second nucleic acid molecule, or a third calculated ensemble standard free energy of a duplex formed through hybridization of the first and second nucleic acid molecules at the reaction temperature and reaction buffer conditions.

3. The method of claim 1, wherein the bioinformatic features comprise one or more features based on a first calculated standard free energy of a minimum free energy structure (mfe) of the first nucleic acid molecule, a second calculated standard free energy of the mfe of the second nucleic acid molecule, or a third calculated standard free energy of the mfe of a duplex formed through hybridization of the first and second nucleic acid molecules at the reaction temperature and reaction buffer conditions.

4. The method of claim 1, wherein the bioinformatic features comprise one or more features based on a difference between a calculated ensemble standard free energy and a calculated standard free energy of a mfe of a duplex formed through hybridization of the first and second nucleic acid molecules at the reaction temperature and reaction buffer conditions.

5. The method of claim 1, wherein the bioinformatic features comprise one or more features based on a calculated standard free energy of a strongest-binding N nucleotide subsequence of the first nucleic acid molecule at the reaction temperature and reaction buffer conditions.

6. The method of claim 1, wherein the bioinformatic features comprise one or more features based on a calculated maximum probability of a N nucleotide subsequence of the first nucleic acid molecule being all in unpaired states at equilibrium.

7. The method of claim 1, wherein the bioinformatic features comprise one or more features based on a calculated maximum probability-weighted standard free energy of binding of a N nucleotide subsequence of the first nucleic acid molecule being all in unpaired states at equilibrium.

8. The method of claim 5, wherein N has a value of 3, 4, 5, 6, 7, or 8.

9. The method of claim 8, wherein feature weight coefficients a and b of a linear transformation are calculated on Xth and Yth percentile values of untransformed feature values in the database.

10. The method of claim 9, wherein the Xth percentile value is between 5 and 40, and the Yth percentile value is between 60 and 95.

11. The method of claim 1, wherein the distances between the plurality of feature values comprises Euclidean distances.

12. The method of claim 1, wherein the distances between the plurality of feature values comprises a Hamming distance.

13. The method of claim 1, wherein weights of value instances are calculated as InstanceWeight=c·exp(−Distance/D), where and c and D comprise constants identical in value for all value instances.

14. The method of claim 1, wherein the weighted average is calculated as WeightedAverage=ΣInstanceWeight·log (RateConstant).

15. A computing system, comprising a processor, the processor configured to predict a rate constant for a hybridization reaction between a first sequence and a second sequence by:
   storing a database consisting of ten or less columns for storing bioinformatics features of the desired hybridization reaction, each column storing a different bioinformatics feature, wherein rows of the database are written based on data acquired by performing hybridization experiments on a plurality of hybridization reactions having known rate constants, the data acquired consisting of values for the rows storing the bioinformatics features;
   calculating a plurality of feature values for a number of bioinformatic features of the hybridization reaction;

calculating distances between the plurality of feature values and corresponding database rate constant values stored in the database;

calculating a weighted average of a logarithm of the corresponding database rate constant values, with larger weights assigned to value instances having values closer in distance to the plurality of feature values of the hybridization reaction;

providing the weighted average as a predicted logarithm of the rate constant of the hybridization reaction; and selecting at least one candidate probe sequence to use with a target sequence from a plurality of probe sequences based on the predicted logarithm of the rate constant.

16. The computing system of claim 15, wherein the processor is configured to generate a set of candidate probe sequences that are complementary to a target nucleic acid sequence, wherein the hybridization reaction comprises the target nucleic acid sequence, and wherein the target nucleic acid sequence comprises the first sequence.

17. The computing system of claim 16, wherein the processor is configured to predict a predicted hybridization rate constant for each of the set of the candidate probe sequences and to select one or more of the set of the candidate probe sequences if the predicted hybridization rate constant is in a top Z %.

18. The computing system of claim 17, wherein the top Z % comprises 1, 2, 5, 10, 20, or a combination thereof.

19. The computing system of claim 15, wherein the first sequence comprises a target sequence and the second sequence comprises a probe sequence.

20. The system of claim 15, wherein the bioinformatics features of the desired hybridization reaction are based on one or more of:
a calculated ensemble standard free energy of the first sequence;
a calculated ensemble standard free energy of the second sequence;
a calculated ensemble standard free energy of a duplex formed through hybridization of the first sequence and second sequence at predetermined temperature and buffer conditions;
a calculated standard free energy of a minimum free energy structure (mfe) of the first sequence;
a calculated standard free energy of a mfe of the second sequence;
a calculated standard free energy of a mfe of a duplex formed through hybridization of the first sequence and second sequence at predetermined temperature and buffer conditions;
a difference between a calculated ensemble standard free energy and a calculated standard free energy of a mfe of a duplex formed through hybridization of the first sequence and second sequence at predetermined temperature and buffer conditions;
a calculated standard free energy of strongest-binding N nucleotide subsequence of the first sequence at predetermined temperature and buffer conditions;
a calculated maximum probability of a N nucleotide subsequence of the first sequence being all in unpaired states at equilibrium; and
a calculated maximum probability-weighted standard free energy of binding of a N nucleotide subsequence of the first sequence being in all in unpaired states at equilibrium, or a combination thereof.

21. A tangible, non-transitory computer readable medium comprising executable instructions, the instructions configured to:
store a database consisting of ten or less columns for storing bioinformatics features of a desired hybridization reaction, each column storing a different bioinformatics feature, wherein rows of the database are written based on data acquired by performing hybridization experiments on a plurality of hybridization reactions having known rate constants, the data acquired consisting of values for the rows storing the bioinformatics features;
calculate a plurality of feature values for a number of bioinformatic features of the desired hybridization reaction between a first sequence and a second sequence;
calculate distances between the plurality of feature values and corresponding database rate constant values stored in the database;
calculate a weighted average of a logarithm of the database rate constant values, with larger weights assigned to value instances having values closer in distance to the plurality of feature values of the desired hybridization reaction;
provide the weighted average as a predicted logarithm of the rate constant of the desired hybridization reaction; and
select at least one candidate probe sequence to use with a target sequence from a plurality of probe sequences based on the predicted logarithm of the rate constant.

22. The tangible, non-transitory computer readable medium of claim 21, wherein weights of value instances are calculated as InstanceWeight=c·exp(−Distance/D), where and c and D comprise constants identical in value for all value instances.

23. The tangible, non-transitory computer readable medium of claim 21, wherein the bioinformatics features of the desired hybridization reaction are based on one or more of:
a calculated ensemble standard free energy of the first sequence;
a calculated ensemble standard free energy of the second sequence;
a calculated ensemble standard free energy of a duplex formed through hybridization of the first sequence and second sequence at predetermined temperature and buffer conditions;
a calculated standard free energy of a minimum free energy structure (mfe) of the first sequence;
a calculated standard free energy of a mfe of the second sequence;
a calculated standard free energy of a mfe of a duplex formed through hybridization of the first sequence and second sequence at predetermined temperature and buffer conditions;
a difference between a calculated ensemble standard free energy and a calculated standard free energy of a mfe of a duplex formed through hybridization of the first sequence and second sequence at predetermined temperature and buffer conditions;
a calculated standard free energy of strongest-binding N nucleotide subsequence of the first sequence at predetermined temperature and buffer conditions;
a calculated maximum probability of a N nucleotide subsequence of the first sequence being all in unpaired states at equilibrium; and a calculated maximum probability-weighted standard free energy of binding of a N nucleotide subsequence of the first sequence being in all in unpaired states at equilibrium, or a combination thereof.

24. The tangible, non-transitory computer readable medium of claim 21, wherein the instructions are configured to generate a set of candidate probe sequences that are complementary to a target nucleic acid sequence, wherein the desired hybridization reaction comprises the target nucleic acid sequence, and wherein the target nucleic acid sequence comprises the first sequence.

25. The tangible, non-transitory computer readable medium of claim 21, wherein the instructions configured to predict a predicted hybridization rate constant for each of the set of the candidate probe sequences and to select one or more of the set of the candidate probe sequences if the predicted hybridization rate constant is in a top Z %.

* * * * *

SEQUENCE LISTING

```
<160> NUMBER OF SEQ ID NOS: 109

<210> SEQ ID NO 1
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 1
aagatggtga gtgccatctt aaaacttact ggagat                            36

<210> SEQ ID NO 2
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 2
ttttcacaaa gatggtgagt gccatcttaa aactta                            36

<210> SEQ ID NO 3
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 3
tgttcaactt ttcacaaaga tggtgagtgc catctt                            36

<210> SEQ ID NO 4
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 4
ttccctcctg gaaagccgaa gcttagagct tcacgt                            36

<210> SEQ ID NO 5
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 5
acttccctcc tggaaagccg aagcttagag cttcac                            36
```

<210> SEQ ID NO 6
<211> LENGTH: 36
<212> TYPE: DNA
<213> ORGANISM: Unknown
<220> FEATURE:
<223> OTHER INFORMATION: Description of Unknown:
     Target sequence

<400> SEQUENCE: 6
agacttccct cctggaaagc cgaagcttag agcttc                                     36

<210> SEQ ID NO 7
<211> LENGTH: 36
<212> TYPE: DNA
<213> ORGANISM: Unknown
<220> FEATURE:
<223> OTHER INFORMATION: Description of Unknown:
     Target sequence

<400> SEQUENCE: 7
tgggatgtcc ccgggggacc gtgcagcctg cccctg                                     36

<210> SEQ ID NO 8
<211> LENGTH: 36
<212> TYPE: DNA
<213> ORGANISM: Unknown
<220> FEATURE:
<223> OTHER INFORMATION: Description of Unknown:
     Target sequence

<400> SEQUENCE: 8
gttgggatgt ccccggggga ccgtgcagcc tgcccc                                     36

<210> SEQ ID NO 9
<211> LENGTH: 36
<212> TYPE: DNA
<213> ORGANISM: Unknown
<220> FEATURE:
<223> OTHER INFORMATION: Description of Unknown:
     Target sequence

<400> SEQUENCE: 9
ggagttggga tgtccccggg ggaccgtgca gcctgc                                     36

<210> SEQ ID NO 10
<211> LENGTH: 36
<212> TYPE: DNA
<213> ORGANISM: Unknown
<220> FEATURE:
<223> OTHER INFORMATION: Description of Unknown:
     Target sequence

<400> SEQUENCE: 10
caggcgtgag ccaccacgcc tggccaatta tgtaat                                     36

<210> SEQ ID NO 11
<211> LENGTH: 36
<212> TYPE: DNA
<213> ORGANISM: Unknown
<220> FEATURE:
<223> OTHER INFORMATION: Description of Unknown:
     Target sequence

<400> SEQUENCE: 11
gggattacag gcgtgagcca ccacgcctgg ccaatt                                     36

```
<210> SEQ ID NO 12
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 12
aagtgctggg attacaggcg tgagccacca cgcctg                              36

<210> SEQ ID NO 13
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 13
acataaaaat tagccaggtg tggtggtggg cacctg                              36

<210> SEQ ID NO 14
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 14
aattagccag gtgtggtggt gggcacctgt aatctc                              36

<210> SEQ ID NO 15
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 15
caggtgtggt ggtgggcacc tgtaatctca gctact                              36

<210> SEQ ID NO 16
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 16
ttgggaggcc aaggcaggca gatcacctga ggtcag                              36

<210> SEQ ID NO 17
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 17
actttgggag gccaaggcag gcagatcacc tgaggt                              36

<210> SEQ ID NO 18
```

```
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 18
agcactttgg gaggccaagg caggcagatc acctga                              36

<210> SEQ ID NO 19
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 19
acatttagag tagtccttgg agattttatg gagatg                              36

<210> SEQ ID NO 20
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 20
aagttgcggt tgtggtgatt ttggcttaat gtgttc                              36

<210> SEQ ID NO 21
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 21
tcacaagact aaagataatt aaaaagaaaa ccacag                              36

<210> SEQ ID NO 22
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 22 gaaacccat ctctaccaaa aatataaaaa ctagct                               36

<210> SEQ ID NO 23
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 23
cttagttgga gtttggggta tttgaaaacg tcatgc                              36

<210> SEQ ID NO 24
<211> LENGTH: 36
```

```
<212> TYPE: DNA
<213> ORGANISM: Unknown
<220> FEATURE:
<223> OTHER INFORMATION: Description of Unknown:
      Target sequence

<400> SEQUENCE: 24
tctggtgggg aatttaaaaa tgcatcctgg aaatcc                              36

<210> SEQ ID NO 25
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 25
cttggagatt ttatggagat ggtgagcaca aggtaa                              36

<210> SEQ ID NO 26
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 26
gcacttctct tgaattcctt tatagatgta cagttt                              36

<210> SEQ ID NO 27
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 27
acaatagtga aactccgtct caaaaagaaa aaaagt                              36

<210> SEQ ID NO 28
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 28
aagattaaat ggttaggtct ttttaaaagt tgcggt                              36

<210> SEQ ID NO 29
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 29
aaatattcat tcatgagctc ttttggcaat ccgtca                              36

<210> SEQ ID NO 30
<211> LENGTH: 36
<212> TYPE: DNA
```

```
<213> ORGANISM: Unknown
<220> FEATURE:
<223> OTHER INFORMATION: Description of Unknown:
      Target sequence

<400> SEQUENCE: 30
ttttattttt atttttttga gataatttca ctcttg                                  36

<210> SEQ ID NO 31
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 31
ggtcgcccca ggagatcaca ggtaggggag ttggga                                  36

<210> SEQ ID NO 32
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 32
ctccaattca gtaaatggta tcactgttta cccctt                                  36

<210> SEQ ID NO 33
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 33
atccgtccac ttgccttggc tccccaaagt gctggg                                  36

<210> SEQ ID NO 34
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 34
aggttatctt agttggagtt tggggtattt gaaaac                                  36

<210> SEQ ID NO 35
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 35
gctatcattt ccctcagaaa gctaagtaaa tttact                                  36

<210> SEQ ID NO 36
<211> LENGTH: 36
<212> TYPE: DNA
<213> ORGANISM: Unknown
```

-continued

<220> FEATURE:
<223> OTHER INFORMATION: Description of Unknown:
      Target sequence

<400> SEQUENCE: 36
aaatgttttt ggtattaaag aatatttggt ataaag                     36

<210> SEQ ID NO 37
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 37
attcatttct caaagagtaa aagtgcaggt tgtatg                     36

<210> SEQ ID NO 38
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 38
ccaggttatc ttagttggag tttggggtat ttgaaa                     36

<210> SEQ ID NO 39
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 39
tattcaggga cagtgtagca agtagcttac aagggg                     36

<210> SEQ ID NO 40
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 40
aattttacca taagttttac ctattcgtaa gttggc                     36

<210> SEQ ID NO 41
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 41
tgtctcttct gaaactggag tttgaattag gttccc                     36

<210> SEQ ID NO 42
<211> LENGTH: 36
<212> TYPE: DNA
<213> ORGANISM: Unknown
<220> FEATURE:

<223> OTHER INFORMATION: Description of Unknown:
      Target sequence

<400> SEQUENCE: 42
tataattaca tactgaatta tttcatgcat agtctg                                   36

<210> SEQ ID NO 43
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 43
gctcttttgg caatccgtca tcagtatatt ctgaaa                                   36

<210> SEQ ID NO 44
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 44
tacattatat tgcccttcag aatagattcc agttcc                                   36

<210> SEQ ID NO 45
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 45
tggagtttgg ggtatttgaa aacgtcatgc cttcag                                   36

<210> SEQ ID NO 46
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 46
gcccagctta ttttgtgttt ttagtagaga cagggt                                   36

<210> SEQ ID NO 47
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 47
ccaagcgggg agcattcgag tggagcccgc gctggg                                   36

<210> SEQ ID NO 48
<211> LENGTH: 36
<212> TYPE: DNA
<213> ORGANISM: Unknown
<220> FEATURE:
<223> OTHER INFORMATION: Description of Unknown:

-continued

Target sequence

<400> SEQUENCE: 48
aggaggactg cttgtgccca gaagttcgag gctgca                36

<210> SEQ ID NO 49
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 49
aactttgtct cccacataag tctcttctag gcactg                36

<210> SEQ ID NO 50
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 50
ttttaaaaag gacatttcta tcagggatat atacct                36

<210> SEQ ID NO 51
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 51
ctggggctgt tctcatactg gggctttctg ccccag                36

<210> SEQ ID NO 52
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 52
gttctcatac tggggctttc tgccccagga ccacac                36

<210> SEQ ID NO 53
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 53
ctggggcttt ctgccccagg accacacctt cctgtc                36

<210> SEQ ID NO 54
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 54
gctccagtgc accccaggct tcgtggccag cctggg          36

<210> SEQ ID NO 55
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 55
gtgcacccca ggcttcgtgg ccagcctggg aaactg          36

<210> SEQ ID NO 56
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 56
cccaggcttc gtggccagcc tgggaaactg tctcta          36

<210> SEQ ID NO 57
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 57
ctgtgaactt ccctcccagg ccagcagagg gctggc          36

<210> SEQ ID NO 58
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 58
ccctcccagg ccagcagagg gctggctgta gctccc          36

<210> SEQ ID NO 59
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 59
gccagcagag ggctggctgt agctcccagg cgcccc          36

<210> SEQ ID NO 60
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 60
gtgtcaggag cccctctctc cctctcttgg agagag    36

<210> SEQ ID NO 61
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 61
gagcccctct ctccctctct tggagagagt cctgag    36

<210> SEQ ID NO 62
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 62
ctctctccct ctcttggaga gagtcctgag tgcccc    36

<210> SEQ ID NO 63
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 63
ccctgtcacc ccgcttattt tcatttctct ctgcgg    36

<210> SEQ ID NO 64
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 64
tcaccccgct tattttcatt tctctctgcg gagaag    36

<210> SEQ ID NO 65
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 65
ccgcttattt tcatttctct ctgcggagaa gatcca    36

<210> SEQ ID NO 66
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 66
gccatccaat cgagaccctg gtggacatct tccagg					36

<210> SEQ ID NO 67
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 67
atcgagaccc tggtggacat cttccaggag taccct					36

<210> SEQ ID NO 68
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 68
cctggtggac atcttccagg agtaccctga tgagat					36

<210> SEQ ID NO 69
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 69
tttatatata tatatattat atatatataa aaataa					36

<210> SEQ ID NO 70
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 70
ttccatacct tcacaacact tgtgcctccc ccaggg					36

<210> SEQ ID NO 71
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 71
taccttcaca acacttgtgc ctcccccagg gcctct					36

<210> SEQ ID NO 72
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 72
cacaacactt gtgcctcccc cagggcctct ttctca      36

<210> SEQ ID NO 73
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 73
ccctgtactt tccactgccc tacctagatg tccctg      36

<210> SEQ ID NO 74
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 74
gagattttgt cccttcatcc accggcttct agatta      36

<210> SEQ ID NO 75
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 75
ggacttgaca ttttagggtt tttaggtgat tattct      36

<210> SEQ ID NO 76
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 76
acacactgaa ggagctgtag catccaagaa tactag      36

<210> SEQ ID NO 77
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 77
tgtcaacaaa gcacagatgc tctcgctggg gccttg      36

<210> SEQ ID NO 78
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 78
tctgtcctca gtggtcccag gctgcaccca tggcag      36

<210> SEQ ID NO 79
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 79
acccagtctc ggcttcccac caaagccttg tcaggg                          36

<210> SEQ ID NO 80
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 80
agctgcctcc ccctttgggt tttgccagac tccaca                          36

<210> SEQ ID NO 81
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 81
gctccgatgg gggcaacagc agttgggtcc ctgtgg                          36

<210> SEQ ID NO 82
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 82
aatgtgactt gggtccattt gaatccaaag tccctg                          36

<210> SEQ ID NO 83
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 83
ggccgctggt cccggacgaa ctggaagtct gagcag                          36

<210> SEQ ID NO 84
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 84
aggtgagcat gcctgggggt gttggggaga tgcaat                          36

<210> SEQ ID NO 85
<211> LENGTH: 36
<212> TYPE: DNA
<213> ORGANISM: Unknown
<220> FEATURE:
<223> OTHER INFORMATION: Description of Unknown:
    Target sequence

<400> SEQUENCE: 85
taagtgaagt caagttgttc aggggctaa gcccat                              36

<210> SEQ ID NO 86
<211> LENGTH: 36
<212> TYPE: DNA
<213> ORGANISM: Unknown
<220> FEATURE:
<223> OTHER INFORMATION: Description of Unknown:
    Target sequence

<400> SEQUENCE: 86
gagggcaggg ctggggctgt tctcatactg gggctt                             36

<210> SEQ ID NO 87
<211> LENGTH: 36
<212> TYPE: DNA
<213> ORGANISM: Unknown
<220> FEATURE:
<223> OTHER INFORMATION: Description of Unknown:
    Target sequence

<400> SEQUENCE: 87
agccccctat tccggcccaa cccatggcac ccacag                             36

<210> SEQ ID NO 88
<211> LENGTH: 36
<212> TYPE: DNA
<213> ORGANISM: Unknown
<220> FEATURE:
<223> OTHER INFORMATION: Description of Unknown:
    Target sequence

<400> SEQUENCE: 88
gccagccttg cacacacttt gtcctggtga aaggca                             36

<210> SEQ ID NO 89
<211> LENGTH: 36
<212> TYPE: DNA
<213> ORGANISM: Unknown
<220> FEATURE:
<223> OTHER INFORMATION: Description of Unknown:
    Target sequence

<400> SEQUENCE: 89
ctataaatcc atgagcagaa aaatacataa aatgtg                             36

<210> SEQ ID NO 90
<211> LENGTH: 36
<212> TYPE: DNA
<213> ORGANISM: Unknown
<220> FEATURE:
<223> OTHER INFORMATION: Description of Unknown:
    Target sequence

<400> SEQUENCE: 90
tccctgtacc tcctataaaa tcagcatgga gcctgg                             36

```
<210> SEQ ID NO 91
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 91
ccaggcagtg gaggccagcc ctccttggag gggcgg                              36

<210> SEQ ID NO 92
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 92
cctgcatttc gagctcccca gcccccaaca tctggt                              36

<210> SEQ ID NO 93
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 93
tacctttgtg agccccgggc atctgtacct ctttcc                              36

<210> SEQ ID NO 94
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 94
tccgtttcgg ggctcccag aagggtaggg cctgtt                               36

<210> SEQ ID NO 95
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 95
gagcaaactc cccccacccc ctttccaaag cccatt                              36

<210> SEQ ID NO 96
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 96
agtttgccct cttgggcggg gttatcagtg gctggc                              36

<210> SEQ ID NO 97
```

-continued

```
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 97
accccttgcc caggccagac cttcctgcta tcccct                              36

<210> SEQ ID NO 98
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 98
gcctgataca cagccctccc tcccactcct gctccc                              36

<210> SEQ ID NO 99
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 99
cttatggcag cctctccctg cactctctgc ccgtct                              36

<210> SEQ ID NO 100
<211> LENGTH: 36
<212> TYPE: DNA
<213> ORGANISM: Unknown
<220> FEATURE:
<223> OTHER INFORMATION: Description of Unknown:
      Target sequence

<400> SEQUENCE: 100
tctccctcct cagactgggg ctctgagggc aagggg                              36

<210> SEQ ID NO 101
<211> LENGTH: 24
<212> TYPE: DNA
<213> ORGANISM: Unknown
<220> FEATURE:
<223> OTHER INFORMATION: Description of Unknown:
      Target sequence

<400> SEQUENCE: 101
acacacacaa aaaaaagtgt gtgt                                           24

<210> SEQ ID NO 102
<211> LENGTH: 24
<212> TYPE: DNA
<213> ORGANISM: Unknown
<220> FEATURE:
<223> OTHER INFORMATION: Description of Unknown:
      Target sequence

<400> SEQUENCE: 102
acacacactt ttttttgtgt gtgt                                           24

<210> SEQ ID NO 103
<211> LENGTH: 24
```

```
<212> TYPE: DNA
<213> ORGANISM: Unknown
<220> FEATURE:
<223> OTHER INFORMATION: Description of Unknown:
      Target sequence

<400> SEQUENCE: 103
agtcagactt tttttgtgt gtgt                                             24

<210> SEQ ID NO 104
<211> LENGTH: 27
<212> TYPE: DNA
<213> ORGANISM: Unknown
<220> FEATURE:
<223> OTHER INFORMATION: Description of Unknown:
      Target sequence

<400> SEQUENCE: 104
acacacactt aaaattgtgt gtgtccc                                         27

<210> SEQ ID NO 105
<211> LENGTH: 27
<212> TYPE: DNA
<213> ORGANISM: Unknown
<220> FEATURE:
<223> OTHER INFORMATION: Description of Unknown:
      Target sequence

<400> SEQUENCE: 105
acacacactt tttttgtgt gtgtccc                                          27

<210> SEQ ID NO 106
<211> LENGTH: 27
<212> TYPE: DNA
<213> ORGANISM: Unknown
<220> FEATURE:
<223> OTHER INFORMATION: Description of Unknown:
      Target sequence

<400> SEQUENCE: 106
actcagactt tttttgtgt gtgtccc                                          27

<210> SEQ ID NO 107
<211> LENGTH: 28
<212> TYPE: DNA
<213> ORGANISM: Unknown
<220> FEATURE:
<223> OTHER INFORMATION: Description of Unknown:
      Target sequence

<400> SEQUENCE: 107
acataaaaat tagcacataa aaattagc                                        28

<210> SEQ ID NO 108
<211> LENGTH: 35
<212> TYPE: DNA
<213> ORGANISM: Unknown
<220> FEATURE:
<223> OTHER INFORMATION: Description of Unknown:
      Target sequence

<400> SEQUENCE: 108
aatagccagg tgtggtggtg ggcacctgta atctc                                35

<210> SEQ ID NO 109
<211> LENGTH: 36
<212> TYPE: DNA
```

```
<213> ORGANISM: Unknown
<220> FEATURE:
<223> OTHER INFORMATION: Description of Unknown:
      Target sequence

<400> SEQUENCE: 109
aggtgactcc gcctgggggt gttggggagg gagaat                              36
```